United States Patent
Spivack et al.

(10) Patent No.: US 7,141,372 B2
(45) Date of Patent: Nov. 28, 2006

(54) UNIVERSAL RT-COUPLED PCR METHOD FOR THE SPECIFIC AMPLIFICATION OF MRNA

(75) Inventors: Simmon D. Spivack, Nassau, NY (US); Gregory J. Hurteau, Lakewood, CO (US)

(73) Assignee: Health Research Incorporated, Rensselaer, NY (US)

( * ) Notice: Subject to any disclaimer, the term of this patent is extended or adjusted under 35 U.S.C. 154(b) by 472 days.

(21) Appl. No.: 10/342,684

(22) Filed: Jan. 15, 2003

(65) Prior Publication Data

US 2003/0186288 A1 Oct. 2, 2003

Related U.S. Application Data

(60) Provisional application No. 60/349,943, filed on Jan. 18, 2002.

(51) Int. Cl.
*C12Q 1/68* (2006.01)
*C07H 21/02* (2006.01)

(52) U.S. Cl. .............. 435/6; 435/6; 536/23.1

(58) Field of Classification Search ............ None
See application file for complete search history.

(56) References Cited

U.S. PATENT DOCUMENTS 5,262,311 A * 11/1993 Pardee et al. ............. 435/91.2
5,845,267 A 12/1998 Ronen
6,777,180 B1 8/2004 Fisher et al.

OTHER PUBLICATIONS

Ayala, M. et al. New Primer Strategy Improves Precision of Differential Display. 1995, BioTechniques, vol. 18, No. 5, pp. 842-844, 846, 848, 850.*

* cited by examiner

*Primary Examiner*—Gary Benzion
*Assistant Examiner*—Samuel C. Woolwine
(74) *Attorney, Agent, or Firm*—Frommer Lawrence & Haug LLP; Thomas J. Kowalski

(57) ABSTRACT

The invention relates to a novel Universal RT-coupled PCR strategy for the specific detection and accurate quantitation of mRNA. Claimed and disclosed are novel Universal reverse transcription (RT) primers, a specific primer mix containing the Universal RT-primers, a transcript specific forward primer and a reverse PCR primer identical to a unique tag sequence, and methods and kits thereof for avoiding the amplification of genomic DNA and/or pseudogenes.

28 Claims, 20 Drawing Sheets mRNA specific RT primer

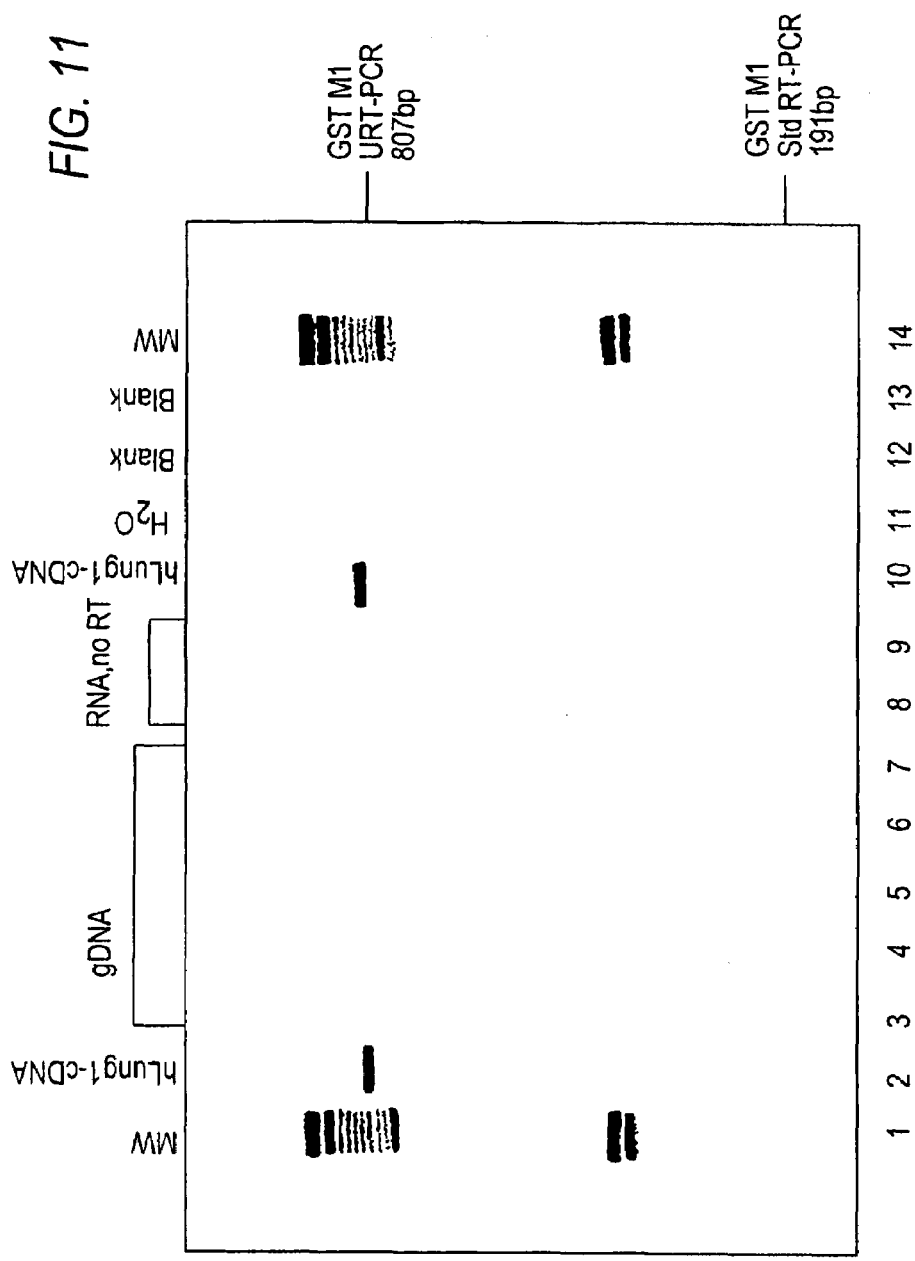

UNIVERSAL RT-COUPLED PCR METHOD FOR THE SPECIFIC AMPLIFICATION OF MRNA

RELATED APPLICATIONS/PATENTS & INCORPORATION BY REFERENCE

This application claims priority from U.S. provisional application Ser. No. 60/349,943, filed Jan. 18, 2002, incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein cited references"), as well as each document or reference cited in each of the herein-cited references (including any manufacturer's specifications, instructions, etc.), is hereby expressly incorporated herein by reference.

STATEMENT OF RIGHTS TO INVENTION MADE UNDER FEDERALLY SPONSORED RESEARCH

This work was supported by the government, in part, by grants from the National Institute of Environmental Health Sciences and the National Cancer Institute (NIEHS-K08 ES0029801; NCI-R21 CA94714). The government may have certain rights to this invention.

FIELD OF THE INVENTION

The present invention relates to a novel Universal RT-coupled PCR strategy for the specific detection and accurate quantitation of mRNA. More specifically, the present invention relates to novel Universal reverse transcription (RT) and polymerase chain reaction (PCR) primers, a specific primer mix containing the Universal RT and PCR primer, a transcript-specific forward PCR primer and a reverse PCR primer identical to a unique tag sequence, and methods and kits thereof for avoiding the amplification of genomic DNA and/or pseudogenes and therefore providing true quantitation of gene expression.

BACKGROUND OF THE INVENTION

The specific amplification of mRNA for the quantitation of gene expression is central to the understanding of a wide range of biological processes, including gene regulation, development, differentiation, senescence, oncogenesis, pathogenesis of disease and many other medically important processes.

The sensitivity of RT-PCR has made it an essential tool of molecular biology for the detection of gene expression. Moreover, with the advent of real-time quantitative PCR technology, transcripts can now be quantitated with precision (Bustin et al., 2000). However, it has been shown that processed pseudogene sequences present in genomic DNA contamination of "RNA" extracts can confound even the most well-designed, standard PCR primers. These genomic DNA sequences are prevalent for highly-expressed "housekeeper" genes, such as β-actin, GAPDH and 36B4. Even small amounts of contaminating genomic DNA can cause false positives by the inadvertent amplification of genomic DNA or pseudogenes (Lion et al., Leukemia 15, 1033–1037, 2001).

Co-amplification of processed pseudogenes in RT-PCR is underreported in the scientific literature. Of the articles that acknowledge the problem, some focus on designing primers to take advantage of the limited sequence differences in the pseudogene sequence versus the mRNA sequence (Lion, Leukemia 15, 1033–1037, 2001; Raff et al. BioTechniques 23:456–460.1997; Kreuzer et al. Clinical Chemistry 45(2), 1999; Shibutani et al. Laboratory Investigation Vol. 80, No 2, p. 199, 2000 and Krauter et al. British Journal of Haematology 107,80–85, 1999). Others rely on DNase treatment to eliminate the genomic DNA signal (Lion, Leukemia 15, 1033–1037, 2001; Ambion Tech Notes Newsletter. Volume 8, Number 1, 2001; Huang et al. BioTechniques Vol. 20, No 6,1012–20, 1996; Bauer et al. BioTechniques 22:1128–32, 1997 and Ivarsson et al. BioTechniques 25:630–36, 1998), while others contend that the amplification of processed pseudogenes is insignificant to the overall signal (Overbergh et al. Cytokine, Vol. 11(4): 305–312, 1999 and Hartel et al. Scandinavian Journal of Immunology 49,649–654,1999).

Traditionally, there have been a number of strategies developed for the isolation of RNA in an attempt to reduce DNA contamination, such as the addition of a DNase digestion step (Raff et al. BioTechniques 23:456–460, 1997; Kreuzer et al. Clinical Chemistry 45(2), 1999; Getting Rid of Contaminating DNA. Ambion Tech Notes Newsletter. Volume 8, Number 1 2001; Huang et al. BioTechniques Vol. 20, No 6,1012–20, 1996; Bauer et al. BioTechniques 22:1128–32, 1997 and Ivarsson et al. BioTechniques 25:630–36, 1998), or passing the total RNA extracted from tissue samples through a PolyA column. Unfortunately, these strategies are unsuitable for optimal gene expression sensitivity, particularly for small samples or low-copy transcripts. Moreover, there are important considerations when using DNase to eliminate DNA contamination (Raff et al. BioTechniques 23:456–460, 1997; Ambion Tech Notes Newsletter, Volume 8, Number 1, 2001; and Lacave et al. British Journal of Cancer 77(5) 694–702, 1998). (1) Inactivation of the DNase must be complete because both reverse transcriptase and Taq polymerase can be degraded by active DNase; (2) failure to completely inactivate DNase can result in diminished or no product formation; and (3) DNase digestion protocols can result in significant RNA loss which is particularly important when attempting to amplify low levels of transcripts or isolating RNA from very small samples (Raff et al. BioTechniques 23:456–460.1997; Kreuzer et al. Clinical Chemistry 45(2). 1999; and Huang et al. BioTechniques Vol. 20, No 6,1012–20, 1996, see FIG. 1).

An alternative to adding further steps to the RNA purification is to design PCR primers that are so-called "mRNA specific". In native genes, individual exons are separated by an intron, and therefore the exon/exon primer-specific sequence does not exist in the coding gene with introns. Two typical strategies for primer design are: 1) To design the primers to span an intron such that the genomic DNA product is larger than the mRNA-derived product, and therefore easily size-distinguishable by visualization on a gel or 2) design an individual primer of a primer pair to span an exon/exon border in the mRNA. These approaches, however, are insufficient to ensure consistent mRNA-specific amplification. Raff et al. (Biotechniques 23:456–460, 1997) developed a quantitative β-actin RT-PCR that does not co-amplify processed β-actin pseudogenes, but maximum primer efficiency requires very specific annealing conditions. Two new sets of primers were designed around small pseudogene-RNA differences that allowed for specific amplification of human and rat β-actin reverse transcribed mRNA but not pseudogene sequences in small tissue samples from biopsies. The forward primer corresponds to the 18- and 20-nucleotide sequences in the 5' untranslated region of exon 1 of human and rat β-actin gene respectively and the reverse primer corresponds to the 23-nt sequence from exon 4 of the human β-actin gene. Kreuzer et al. (Clinical Chemistry, 45:297–300, 1999) also developed a quantitative Taq Man™ PCR specific for human β-actin that relied on a few pseudogene mismatches with the 3' end of the sense (reverse) primer to reportedly avoid amplification of contaminating genomic DNA-encoding pseudogene. However, data demonstrating RNA-specific RT-PCR was not shown in that article.

There have been further efforts to design a so-called RNA-specific RT-PCR (Joo et al. J. Virol. Meth. 100:71–81, 2002; Smith et al. Biotechniques 31:776–782, 2001; Sybesma et al. BioTechniques 31:466–472, 2001; Folz et al. Biotechniques 29:762–768, 2000; Shuldiner et al Gene 91: 139–142, 1990 and Shuldiner et al BioTechniques 11(6): 760–763, 1991). Joo et al. describe a tagged RT-PCR strategy for specifically amplifying viral CMV RNA, which takes advantage of temperature differences between RT and PCR. Limitations include 1) The RT approach is not universal, in that a new RT primer must be designed for each transcript to be amplified, and 2) the corollary is that there is inefficient use of precious total RNA sample required for each separate RT. 3) The RT primer sequence in this system is not specific for poly-A signal, and therefore RNA specificity depends entirely on access to a single strand viral RNA loop at standard RT temperatures. 4) The requirement for rigid reaction parameters, specific to each transcript, is highlighted by the demonstrated need for precise [Mg++] optimization for the system to be RNA- and transcript-specific, in the description and performance data. 5) RT efficiency and PCR efficiency will vary transcript to transcript, given the dual-role-of-primer strategy. 6) The system is not tested for non-viral eukaryotic or mammalian systems.

Smith et al. describe the employment of a tagged, anchored RT-RACE primer used from a commercial source (Clontech), combined with the use of that tag in PCR in a three-step step-in, step-out strategy. Limitations include: 1) The process is very complex. 2) The insertion of the larger generic reverse primer is a separate 35-cycle PCR step. 3) Two steps of a nested PCR strategy for GAPDH is required, which is time and labor expensive. 4) Potential for RT-RACE primer slippage is possible for transcripts, given that poly-T tail can anneal anywhere on the poly-A tail of mRNA with only one mismatch; this would yield multiple size bands for PCR product. 5) Multiple products in the GAPDH and HERV-K demonstration gene products preclude real-time quantitation. 6) Poly-A tails shorter than 30-mer on mRNA transcripts may not anneal the RACE primer, because of the length of the combined overhanging poly-T and 25-mer tag sequence. 7) Sensitivity has not been quantitated.

Folz et al. describe the design of a primer for one single gene that has both RT and PCR functions, depending on temperature parameters programmed into the respective RT and PCR protocols. Limitations include 1) The RT approach is not universal, in that a new RT primer must be designed for each transcript to be amplified, and 2) the corollary is that there is inefficient use of precious total RNA sample required for each separate RT. 3) The design parameters of the system are highly restrictive, preventing design of dual function RT-PCR antisense primers suitable for other transcripts; the poly-T tail demands a high GC transcript-specific design for nucleotide balance and the prevention of self-annealing. This would make the few possible primers inefficient, or completely unsuitable, for many transcripts and cDNAs. 4) The gene-specific 3' end of the dual-function primer may readily anneal to gDNA pseudogene on PCR cycling, as could the poly-T tail, as many processed pseudogenes contain poly-A tails. 5) The system was reported for only one transcript; no data is available on others.

Sybesma et al. describe a RT-PCR employing tag-extended RT primers using temperature-gradient PCR, and Shuldiner et al. (1990 and 1991) describe an RNA template-specific PCR (RS-PCR) to reduce false positives. However the RT-PCR used by these groups have a number of limitations as follows: 1) The RT primers used are transcript-specific, not Universal for all transcripts; therefore new primers have to be designed for each transcript; 2) The PCR extension times need to be changed for each reaction according to the transcript being amplified; 3) The RNA template is consumed quickly as new RNA and reverse transcription is required for every new transcript; and, 4) The procedure requires multiple cumbersome steps.

Lastly, another approach to isolate RNA is to ignore the pseudogene contribution to the overall signal based on the assumption that the number of mRNA copies for an expressed gene greatly exceeds that of the pseudogene and therefore makes its contribution insignificant (Lacave et al. British Journal of Cancer 77(5) 694–702, 1998; Shibutani et al. Laboratory Investigation Vol. 80, No 2, pg. 199, 2000; Krauter et al. British Journal of Haematology 107, 80–85, 1999; Overbergh et al. Cytokine, Vol. 11(4): 305–312, 1999 and Hartel et al. Scandinavian Journal of Immunology 49,649–654, 1999). There are a number of potential problems with this approach. First, the mRNA: genomic DNA ratio may be low, simply as a result of low-copy transcription, characteristic of many native and nonetheless physiologically important transcripts. Second, RNA is more readily degraded than DNA, in part because RNase is ubiquitous. Even if the mRNA to genomic DNA pseudogene ratio is initially very high in the cell, the RNA can be degraded very rapidly from the point of tissue collection up to the end of cDNA synthesis. Consequently the cDNA: genomic DNA ratio after cDNA synthesis may be artificially low compared to original mRNA levels. Finally, the target gene of interest may not be expressed in all cell types. Tissue samples used for RNA isolation may contain many different cell types and the transcript of interest may only be expressed in a small number of these cells, for example epithelial cells. Genomic DNA (and therefore pseudogenes) is present in all cells of a sample, both mesenchymal and epithelial. Therefore, the contribution of PCR product derived from the contaminating genomic DNA pseudogene in the "RNA" sample may be very significant in tissue samples containing several cell types.

An approach that has been routinely used for the determination of mRNA levels is measuring all target transcripts against a constitutively expressed internal reference gene known as a "housekeeping gene", where mRNA expression of the transcript is constant. As previously noted, however, many of the highly expressed housekeeper genes including β-actin and glyceraldehyde-3-phosphate dehydrogenase (GAPDH) have additional related sequences nearby or remotely in the genome called "processed pseudogenes" (Raff et al. BioTechniques 23:456–460, 1997; Kreuzer et al.

Clinical Chemistry 45(2), 1999; Mighell et al. FEBS Letters 468:109–114, 2000; NG et al. Molecular and Cellular Biology 5(10): 2720–32, 1985 and Taylor et al. Br J Haematolog 86: 444–5, 1994). Pseudogenes typically lack promoters or introns, making cDNA primer design that distinguishes cDNA from genomic-derived DNA sequences extraordinarily challenging, and somewhat impractical for high throughput applications (Raff et al. BioTechniques 23:456–460, 1997 and Kreuzer et al. Clinical Chemistry 45(2), 1999). This is particularly true for RNA samples derived from tissues where there is a substantial number of "non-target gene-expressing cells" (e.g. lung fibroblast/mesenchymal cells), mixed in with cells or tissue expressing the gene of interest (e.g. lung epithelial cells). Designing new PCR primers is possible but it remains very difficult to design reliable, cDNA-specific PCR primers or other cDNA-specific amplification strategies in the presence of a pseudogene (Raff et al. BioTechniques 23:456–460, 1997; Kreuzer et al. Clinical Chemistry 45(2), 1999 and Taylor et al. Br J Haematolog 86: 444–5, 1994). Finally, finding non-pseudogene-encoded housekeeper genes is another approach to the pseudogene-for-reference genes problem. Although housekeeping genes such as 28S ribosomal RNA can be good candidates, they are overwhelmingly plentiful, and therefore inadequate for providing a true reflection of RNA degradation, particularly as it affects low-copy number transcripts.

In conclusion, none of above strategies to-date have been successful as a true assay of gene expression without compromising the total RNA yield, specific, efficient and facile amplification of an RNA transcript, or accurate quantitation of the original mRNA transcript.

Therefore it is clear that there exists a need in the art for improved methods of selectively amplifying nucleic acids, especially mRNA, whereby the methods can achieve a high degree of amplification from a limited amount of mRNA and which simultaneously avoids genomic amplification often introduced by other amplification methods. The present invention is believed to satisfy this need and to provide other related advantages.

The present invention provides an improved strategy for the specific amplification of mRNA in total RNA extracts, regardless of sample contamination with genomic DNA. Moreover, the present strategy makes a quantitative evaluation of gene expression RNA-specific while preserving the sensitivity of standard RT-PCR techniques.

Citation of a reference herein shall not be construed as an admission that such reference is prior art to the present invention. In addition, each document or reference cited in this application, are hereby expressly incorporated herein by reference as well as each document or reference cited in each of the herein-cited documents or references, are hereby expressly incorporated herein by reference.

OBJECTS AND SUMMARY OF THE INVENTION

The present invention in an embodiment provides a Universal reverse transcription (RT) primer having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=21 and X having the nucleotide sequence 5'-AAC GAG ACG ACG ACA GAC-3' (SEQ ID No. 20).

The present invention in another embodiment provides a primer set having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=21 and X having the nucleotide sequence 5'-AAC GAG ACG ACG ACA GAC-3' (SEQ ID No. 20) a forward primer and at least one reverse primer identical to X.

In regard to this, the invention further provides a method of selectively amplifying mRNA wherein genomic DNA amplification is avoided comprising reverse transcribing a mRNA template using a primer set having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=21 and X having the nucleotide sequence 5'-AAC GAG ACG ACG ACA GAC-3' (SEQ ID No. 20) wherein X remains unbound to said mRNA template but integrated into each cDNA molecule synthesized, thereby 5' tagging the mRNA-derived cDNA sequences comprising X, thereby allowing for selective amplification of mRNA-derived cDNA in subsequent PCR reactions.

The present invention thus further provides a method for the amplification of multiple different transcripts from tissue-derived RNA sample comprising reverse transcribing a mRNA template using a primer set having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=2 and X having the nucleotide sequence 5'-AAC GAG ACG ACG ACA GAC-3' (SEQ ID No. 20), wherein X is specific for all transcript-derived cDNA sequences, thereby allowing for subsequent PCR amplification of multiple different transcripts. A common reverse PCR primer X can be used for any transcript that undergoes reverse transcription-integration of this tag. The poly-T section of the Universal RT primer ensures that virtually all mRNA transcripts are converted to cDNA, and this tag is integrated.

The present invention further provides a method for constructing a cDNA library from a population of mRNA molecules in a sample, wherein the primer set having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=21 and X having the nucleotide sequence 5'-AAC GAG ACG ACG ACA GAC-3' (SEQ ID No. 20), allows for the selective amplification of a plurality of mRNAs in the sample wherein genomic DNA amplification is avoided.

The present invention still further provides a method for selectively amplifying mRNA in a cell population comprising steps of reverse transcribing a mRNA template using a primer set having the formula 3'-NVVT$_n$X-5', wherein N is equal to all base combinations, V=A, C, or G, C, advantageously n=16, 17, 18, 19, 20, 21, 22, 23, 24, 25 or 26 and preferably n=21 and wherein X remains unbound to said mRNA template but integrated into each cDNA molecule synthesized, thereby 5' tagging the mRNA-derived cDNA sequences with X, thereby selectively allowing for the amplification of mRNA in a subsequent PCR reaction and thereby tagging reverse-transcribed cDNA.

The present invention also provides a kit for a variety of uses. In addition to instructions, a kit will typically comprise reverse transcriptase. Taq polymerase, and nucleotides which may be labeled, such as with radioactive labels (e.g. $^{14}$C, $^{3}$H, $^{32}$P, Cy3, Cy5, $^{33}$P, $^{35}$S, $^{125}$I, fluorophores, fluorescein, rhodamin and Texas Red, and the like).

Also encompassed by the present invention is a method for obtaining and/or generating gene expression data and/or drug efficacy data comprising subjecting a sample to RT-coupled PCR using the primer set having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=21 and X having the nucleotide sequence 5'-AAC GAG ACG ACG ACA GAC-3' (SEQ ID No. 20) and thereby obtaining and/or generating gene expression data and/or drug efficacy data.

The present invention further provides a method for obtaining and/or generating gene expression data and/or drug efficacy data using the primer set having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=21 and X having the nucleotide sequence 5'-AAC GAG ACG ACG ACA GAC-3' (SEQ ID No. 20) and an automated data acquisition system, and thereby obtaining and/or generating gene expression data and/or drug efficacy data.

The present invention still further provides method of doing business comprising receiving a sample from a client, subjecting said sample to RT-coupled PCR using the primer set having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=21 and X having the nucleotide sequence 5'-AAC GAG ACG ACG ACA GAC-3' (SEQ ID No. 20) and thereby generating expression data and/or drug efficacy data from said sample, and transmitting said expression data and/or drug efficacy data to said client.

The terms "comprises", "comprising", and the like can have the meaning ascribed to them in U.S. Patent Law and can mean "includes", "including" and the like.

These and other embodiments are disclosed or are obvious from and encompassed by, the following Detailed Description.

BRIEF DESCRIPTION OF THE FIGURES

The following Detailed Description, given by way of example, but not intended to limit the invention to specific embodiments described, may be understood in conjunction with the accompanying Figures, incorporated herein by reference, in which:

In FIG. 4A, "total RNA" from a single sample (16T) is tested in duplicate, under the two conditions. In FIG. 4B, two different "total RNA" samples (58T, 58NT) are tested in duplicate under each of the two conditions. In the real-time monitoring of the intercalation of SYPBR-Green® dye by increasing amounts of double stranded DNA product as these PCR reactions proceed, circles (○) correspond to for β-actin PCR-only reactions, and diamonds (◇), correspond to β-actin standard RT-PCR. Data is tabulated in Table 2.

In FIG. 10A filled and empty circles correspond to URT-PCR, and filled and empty triangles correspond to oligo dT-RT-PCR. In FIG. 10B circles and triangles correspond to URT-PCR, and squares and diamonds correspond to oligo dT-RT-PCR. Data is tabulated in Table 3.

FIG. 11 shows an agarose gel illustrating the specificity of the GST M1 Universal RT-PCR primer set compared to GST-M1 standard oligo dT-RT and standard-design PCR primers for mRNA detection. Lane 1=MW marker, lane 2=human lung1 cDNA, lanes 3–7=human genomic DNA; lanes 8, 9=total "RNA" extract (no RT), lane 10=human lung1 cDNA, lane 11=H$_2$O, lane 12, 13=blank, and lane 14=MW marker.

DETAILED DESCRIPTION

Introduction

Figure 8:
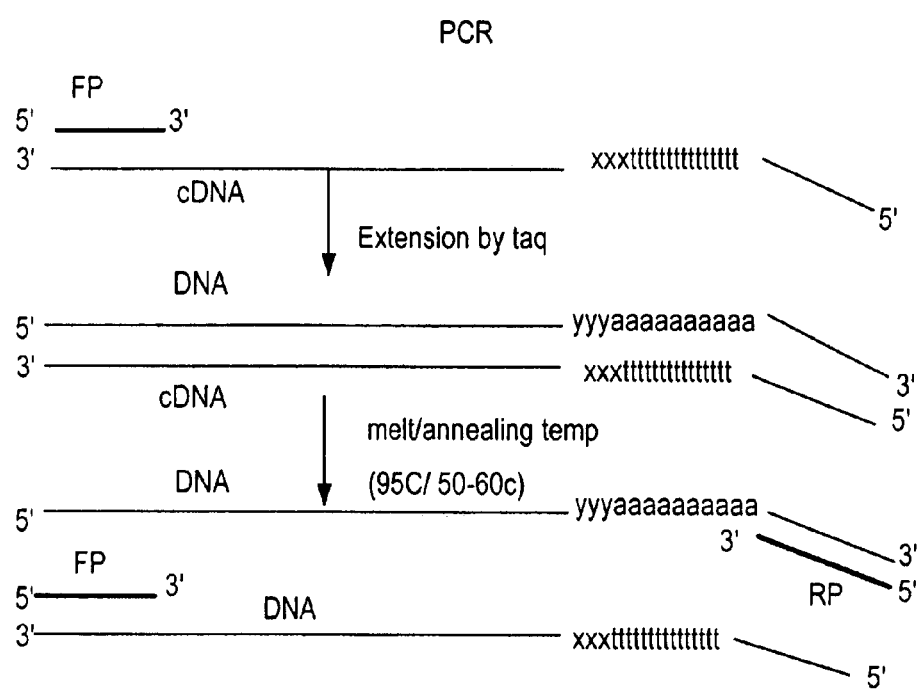
FIG. 8 shows a schematic diagrammatic representation of the annealing of the transcript-specific forward primer (FP) and the Universal reverse PCR primer (RP) to the newly synthesized tagged cDNA during the PCR process.

The present invention relates to "Universal RT-coupled PCR", a novel PCR strategy that takes advantage of the poly-A tail of processed mRNA, and uses novel "Universal RT primers" that comprise a unique 5' tag sequence that does not occur in the genome of the organism being studied (for example the human genome), a poly-T midsection, and a 3' anchor to avoid slippage. These 5' tag-enhanced "Universal RT primers" reliably initiate reverse transcription, and the unique sequence of the 5' tag is then targeted by the PCR primers. The reverse primer used for PCR can be identical to the 5' tag of the Universal RT primer, in which case transcript specificity is conferred by the forward (sense) primer. Reverse PCR primers that are identical to the 5' tag of the Universal RT primer are referred to as "Universal primers" (UR) or "Universal reverse primers" (URP). Genomic DNA or pseudogene amplification is avoided both by limiting reverse transcription to poly-A derived material, and by introducing a genetically engineered sequence tag that does not occur in the human genome and therefore cannot be mimicked by pseudogene sequence. The Universal RT coupled PCR method allows for multiple different transcripts to be amplified from the same tissue derived RNA sample, across multiple experiments on the same subject, similar to oligo dT-based RT strategies. As described herein, avoiding the amplification of genomic DNA or pseudogenes is taken to mean that under normal PCR conditions, there is no non-specific amplification of genomic DNA and/or pseudogenes and therefore no visible band detectable on an agarose gel as shown in FIG. 8.

In the present invention, Universal primer RT design, (for example β-actin, glutathione S-transferases GST-M1 and GST-P1) mRNA transcripts can be amplified alongside non-pseudogene encoded transcripts such as aromatic hydrocarbon receptor (Ahr), cytochrome P450 (CYP1B1 and CYP1A1), glutathione S-transferase GST-T1 and AND (P) H: quinone oxidoreductase (NQ01) (Traver et al. 1997) transcripts from the same RNA sample, in uniplex reactions. Consequently, the there is no need for DNAse treatment of the tissue extract and PCR primer design is simplified.

With genes for which it is known or suspected that related pseudogene sequences exist (such as β-actin, GST-M1 and GST-P1), Universal RT-coupled PCR (using Universal RT primers and Universal reverse primers) can be performed to avoid amplification of those related pseudogene sequences. With genes for which no related pseudogene sequences are believed to exist, (such as Ahr, CYP1B1, CYP1A1, GST-T1, NADPH, and NQ01), either Universal RT-coupled PCR, standard RT-PCR, or RT-PCR in which the reverse transcription reaction uses the Universal RT primer and the PCR reaction used "standard design primers", can be performed.

Construction of the Novel Universal RT Primer

In one embodiment, the RT primers, or sets thereof ("primer sets"), used to perform reverse transcription comprise: a) a 3'"anchor" sequence b) a poly T midsection to anneal to the poly A tail of mRNA, and c) a 5' tag, the sequence of which does not occur in the genome of the species in which gene expression is to be analyzed. The 3' anchor, poly T midsection and 5' tag sequence can be of any length that allows the RT primer to anneal to mRNAs. Primer sets used for any given RT reaction may contain multiple primers with differing sequences of the 3' tag. Although the primer as a whole should anneal or "bind" to mRNA transcripts present in the sample, this "binding" should occur only through the 3' tag and the poly T midsection. The nucleotides of the 5' tag should not anneal to mRNA.

Figure 6:
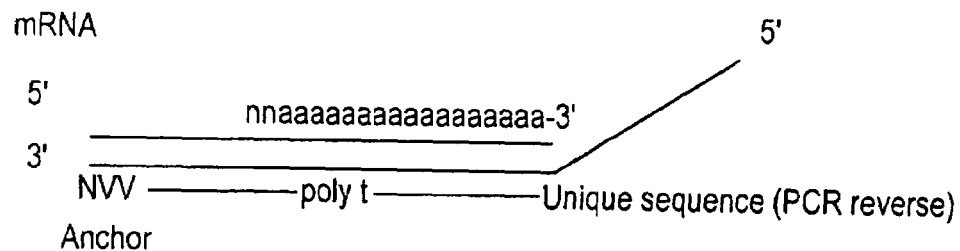
FIG. 6 shows a schematic diagrammatic representation illustrating general structure of the mRNA-specific reverse transcription primer. The 18-base tag at the 5' end of the primer is unique, and does not appear in the human genome.
Figure 7:
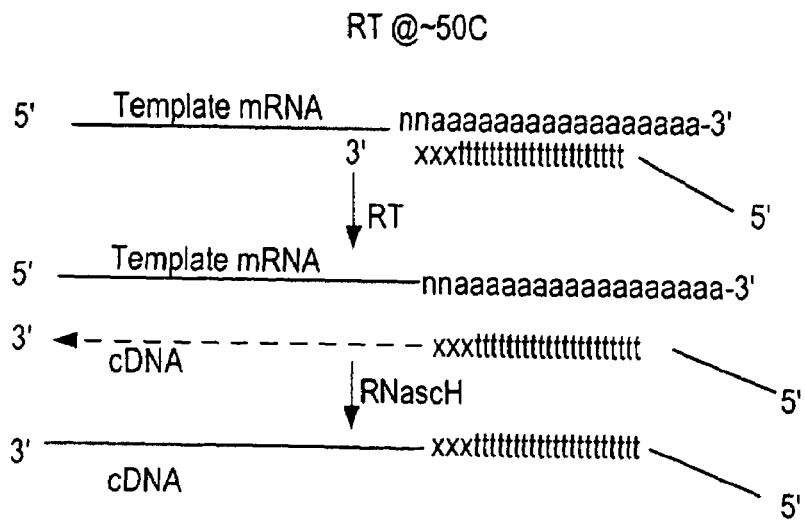
FIG. 7 shows a schematic diagrammatic representation of the annealing process during the Universal reverse transcription process.

In a preferred embodiment, the novel Universal RT primer used for reverse transcription has a 3' three-base anchor that allows the primer to be positioned on the last 3 bases of the transcript specific sequence and covers all possible combinations of the coding 3' end of the mRNA transcript (see FIGS. 6 and 7). This allows RNA binding without slippage, and thereby avoids the generation of cDNA's of various sizes. Also, in this preferred embodiment, the RT primer comprises a 16–26 T's midsection to target the poly-A tail specific to mRNA, advantageously n=16, 17, 18, 19, 20, 21, 22, 23, 24, 25 or 26 and preferably 21 T's to match with the first 21 A's of the polyA tail of mRNA. Preferably, the 5' tag of the RT primer is 18 bases long, and should not be related to any known mRNA or genomic DNA sequence, should be invariate for all targeted mRNA transcripts, and should remain unbound. By "unbound" it is meant that nucleotides of the tag should not anneal to the mRNA template. If the methods of the present invention are used to study human gene expression, it is preferred that the sequence of the 5' tag is the that of SEQ ID No. 20.

The reverse transcriptase extends the 3' end of the primer from the three-base anchor to complement the template mRNA. In the final RT step, RNaseH degrades the original target mRNA, as in standard reverse transcription strategies. Therefore cDNA is produced that is the reverse compliment of the original mRNA with an 18-base tag that is common to all cDNA synthesized with this Universal RT primer set. The RT primer does not anneal to genomic DNA because genomic DNA is double stranded at typical RT temperatures, and the DNA therefore does not incorporate the 18 base tag. Genomic DNA pseudogene amplification in the subsequent PCR is thus avoided (see FIGS. 7 and 8).

The Universal RT primer, like an oligo-dT-RT primer, is designed to specifically initiate the synthesis of cDNA from all the mRNA present in the sample. If there is no genomic DNA-encoded pseudogene, then "standard-design" transcript-specific forward and reverse PCR primers using traditional PCR will suffice. The Universal RT primer of the present invention will prime all mRNA transcripts at the same time, similar to the oligo-dT-RT method. In contrast, if there is a known or suspected genomic DNA pseudogene for the target sequence, the PCR can take advantage of the 18-base tag inserted uniquely in reverse-transcribed sequence at the time of Universal RT, and employ a transcript-specific forward PCR primer paired with the Universal reverse primer, to avoid amplifying genomic DNA-derived pseudogene sequence. Therefore, the system requires minimal adaptation from current RT-PCR methodologies.

Forward PCR Primer

The forward PCR primer can be transcript-specific, i.e., see Table 1, to any particular gene of interest or a degenerate primer to a particular family of common genes. (Compatibility with the reverse PCR primer, be it transcript-specific, degenerate, or Universal, is integrated into the design).

Reverse PCR Primer

The reverse PCR primer can be any suitable primer that will allow amplification of the desired target sequence. Design of such primers is routine to those skilled in the art. In the case of the Universal RT-Coupled PCR methods of the present invention, for amplification of a cDNA suspected of having analogous sequence in genomic DNA in the form of a processed peseudogene, it is preferred that the reverse PCR primer sequence is identical to the tag at the 5' end of the Universal RT primer, or comprises a string of contiguous nucleotides from within the sequence of the 5' tag (See FIG. 8). This "Universal Reverse Primer" (URP or UP) is used in combination with a transcript specific forward PCR primer (FP) to produce a product that is both transcript- and mRNA-specific. In one embodiment, the Universal reverse PCR primer is the 18 bp human sequence, SEQ ID No 20. This sequence been aligned against the human genome and has no exact matches. There are only four (4) sequences in the human genome that have less than 5 mismatches when compared to the primer (each of them has 4 mismatches with genomic DNA template). The chances that the four (4) possible products' molecular sizes are identical to the expected cDNA-derived product size of the target transcript, if indeed these templates can be misprimed at all, to make these products, are considered infinitesimal to zero. The 18-mer tag meets Genetics Computer Group sequence software requirements for optimal primer conditions and has a very good annealing score.

Primer Sets

"Primer sets" as used herein, refers to mixtures of primers having different sequences. For example, the Universal RT primers of the inventions can vary in the sequence of the 3' anchor, and have variable numbers of Ts in the poly-T mid-section. Advantageously, the reverse transcription reactions of the present invention are performed using a mixture or pools of primers with different nucleotides represented at the variable sites. These mixtures of Universal RT primers can be referred to as "primer sets". In addition primer sets may contain any other primers desired. For example, primer set mixtures may additionally include primers suitable for priming cDNA amplification in PCR reactions, such as the Universal reverse primer, or any other forward or reverse primers desired.

Genes Amplified by PCR

Figure 5:
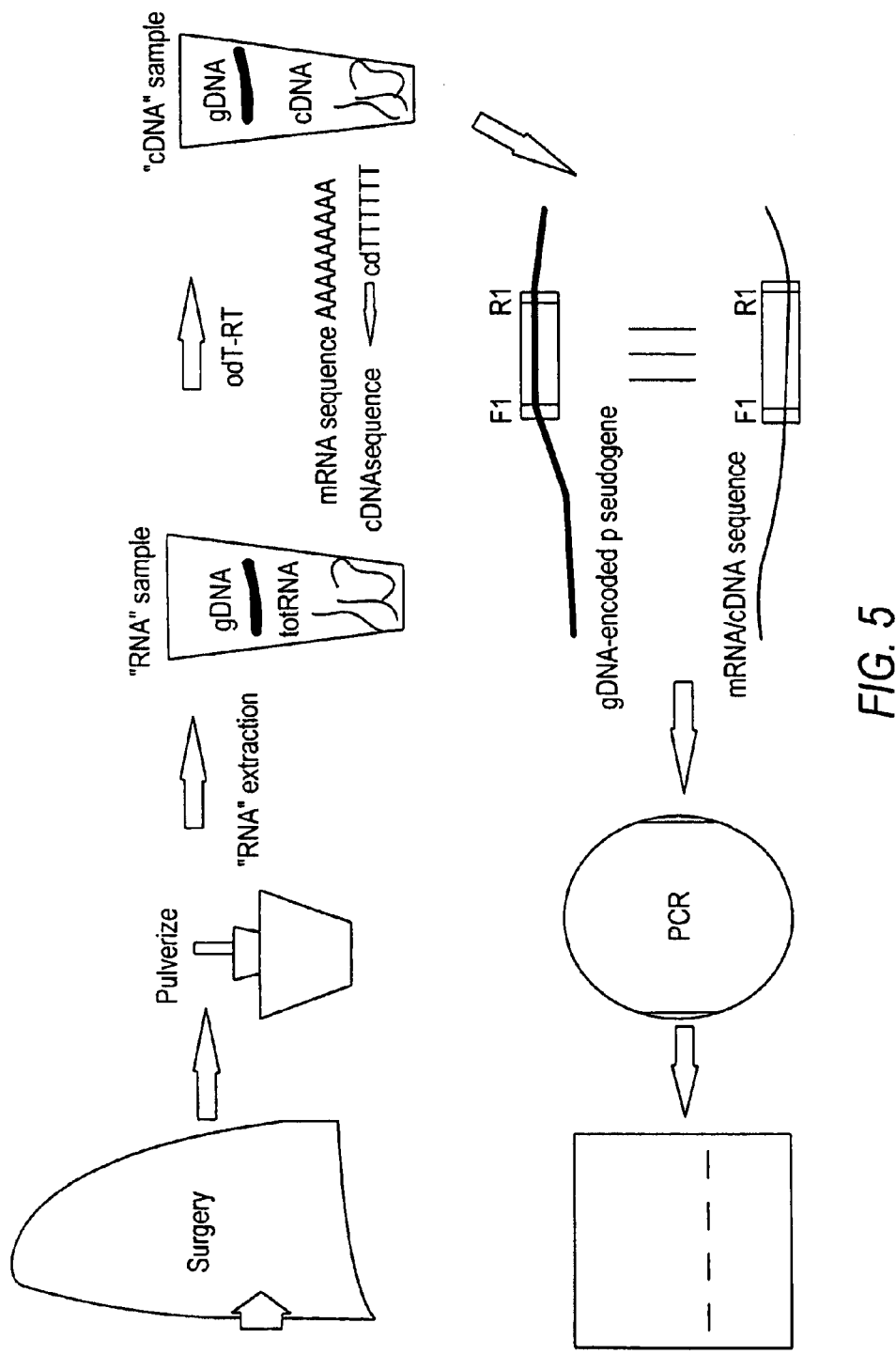
FIG. 5 shows a schematic diagrammatic representation of the pseudogene problem. The β-actin product is derived from a processed pseudogene encoded in genomic DNA, which is a contaminant in the "RNA" extract, and carried through the odT-primed reverse transcription step into the PCR step, where indiscriminant standard-design primers ($F_1R_1$) can amplify the contaminant genomic DNA in the PCR, because it is of virtually identical sequence. There are known annotated genomic DNA-encoded processed pseudogenes that exist for the reference "housekeeper" gene β-actin on multiple chromosomes, as per the Human Genome Project database. Similar processed pseudogenes exist, annotated or not, for other commonly-employed reference "housekeeper" genes used to assay RNA integrity and other target genes of interest also assayed by RT-PCR (see other figures). This presents a major challenge to the validity of such assays.

As described herein, a "pseudogene" is a non-functional sequence present in the genome that shares very close homology to the functional gene. Pseudogenes are present in the genome in two forms: (1) those that are the product of partial or complete gene duplication and (2) "processed pseudogenes" which are double stranded DNA generated from single stranded RNA (retrotransposons). Pseudogenes typically lack 5' promoter sequence and introns (Mighell et al. FEBS Letters 468:109–114, 2000) and amplification can result in product that is identical (or nearly identical) in size and sequence to the expected mRNA product (see FIG. 5).

The term "housekeeper" or "housekeeping gene" will be used interchangeably throughout the application: a "housekeeper" gene is a gene that is expressed in all cell types (preferably with little variation across experimental conditions or time). In RT-PCR the housekeeper gene is amplified in parallel with the gene of interest, to serve as a control for both RNA integrity, and RT and PCR success (Raff et al. BioTechniques 23:456–460, 1997). If RNA integrity is poor for a sample, housekeeper cDNA will not be generated in that sample, but a positive RNA control will successfully demonstrate amplified housekeeper transcript (Kreuzer et al. Clinical Chemistry 45(2), 1999). Alternatively, if housekeeper PCR amplification is not successful despite the Universal expression of the housekeeper gene, RNA isolation, RT and PCR are each suspect (Ambion Tech Notes Newsletter. Volume 8, Number 1, 2001).

RNA integrity is a major issue: RNA is a fragile molecule (far more than DNA), and subject to degradation by ubiquitous RNases found on many surfaces. It can degrade very quickly in tissue or cells selected for RNA isolation. Housekeeper genes can be used as a tool to gauge the success of RNA isolation because housekeeper gene mRNA is present in virtually all cell types and should therefore be present in all successful RNA isolations. Also, the amount of housekeeper gene mRNA isolated should reflect the total RNA isolated and can therefore be used to compare analogous samples from different individuals.

Figure 12:
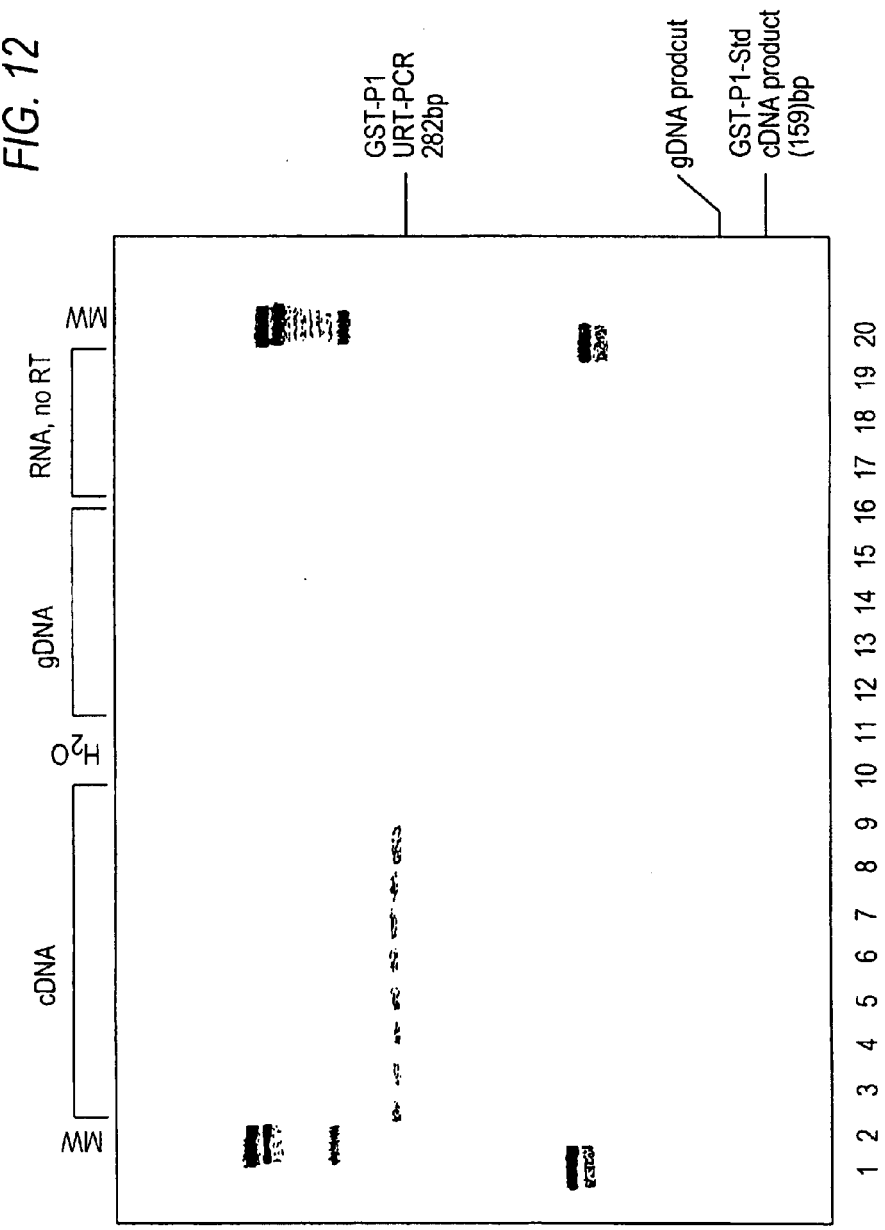
FIG. 12 shows an agarose gel electrophoresis illustrating the specificity of the GST-P1 Universal RT-PCR primer set compared to GST-P1 standard oligo dT-RT and standard-design PCR primers for mRNA detection. Lane 1=MW marker, lanes 2–9=cDNA, lane 10=H$_2$O, lanes 11–15=genomic DNA, lanes 16–19=total "RNA" extract (no RT), and lane 20=MW marker.

For the known housekeeper genes β-actin, GAPDH and acidic ribosomal phosphoprotein PO (36B4), PCR primer design is extraordinarily difficult because pseudogenes have very high sequence similarity to their mRNA counterparts. e.g., the GAPDH pseudogene (X01111) is 96% identical to the mRNA sequence (M17851). Additionally, multiple pseudogenes can be homologous to the same mRNA. In addition to the high homology a processed pseudogene shares with its mRNA counterpart, some genes have multiple processed pseudogenes. β-actin, for example has four pseudogenes (V00481, V00478, D50604, M55014) listed in Genbank, some of which have greater than 90% homology to the β-actin mRNA (X00351). Some genes have been estimated to have as many as 13 related pseudogenes (Mighell et al. FEBS Letters 468:109–114, 2000). Further, many pseudogenes are not annotated as pseudogenes in Genbank, making primer design very difficult indeed. For example, the present inventors have shown that target genes for quantitation studies such as GST-M1 and GST-P1 behave as if a processed pseudogene or sequence highly homologous to the cDNA is present (FIGS. 11 and 12). There are a number of candidates in the human genome for such pseudogene-like sequences (GST-M1, NT_005718.2/Hs3_5875; GST-P1, GB: X65032, NT009458.2/Hs12_9615). Consequently, BLAST searches against Genbank entries must also be supplemented by Blast sequence searches against the entire human genome. For standard design PCR primers, very stringent annealing conditions are required during the PCR for these primers to distinguish between the mRNA transcript and contaminating genomic DNA pseudogenes. If mRNA specific primers can indeed be designed, they often differ from the pseudogene by only a few bases (Raff et al. BioTechniques 23:456–460,1997; Kreuzer et al. Clinical Chemistry 45(2), 1999 and Trummer et al. Journal of Hematotherapy & Stem Cell Research 9:275–284, 2000). This high sequence homology of the pseudogene compared to its mRNA counterpart means that primers must be designed to very specific regions of the mRNA sequence, regions that may not be optimal for efficient RT-PCR (i.e. unfavorable GC content, secondary structure, etc.) A consequence is suboptimal primers that must discriminate from a sequence that is nearly identical to the target. These suboptimal primers will only function under stringent reaction conditions that are difficult to replicate, are limiting, and are contrary to the idea of a Universally applicable housekeeper gene for a quantitation standard for a wide array of comparison transcript targets of interest.

The Universal RT-coupled PCR of the present invention can be applied to improve methods of detecting, isolating and quantitating nucleic acid sequences that vary in abundance among different cell populations, such as in comparing mRNA expression among different tissues or within the same tissue, according to physiologic state. The cell population may be, e.g., from a human tissue, such as blood, brain, spleen, bone, liver, prostate, mammary, heart, kidney, vascular, lung, testis, intestine, muscle, pituitary, endocrine glands, lymph node and dispersed primary cells. The tissue may be an embryonic or fetal tissue. The cell population may be a few cells, or up to 100 to 1,000,000 cells or more, as desired.

Reference Sequences and PCR Primer Design

PCR primers were designed from their DNA sequences (obtained from GenBank® (GB) and EMBL (emb) under accession numbers: X00351, J00074, M10278, M10277, E00829.1 for β-actin; accession numbers: M17851, M33197 for GAPDH; accession number: NT 005274.1 for 36B4; accession number: X02612 for CYP1A1; accession number: U56438 for CYP1B1; accession numbers: X68676, J03817 for GST-M1; accession number: M24485 for GST-P1 using Genetics Computer Software (Madison, Wis.) and synthesized and purified by high performance liquid chromatography at the Molecular Genetics Core Facility (Wadsworth Center, New York State Department of Health, Albany, N.Y., USA). See Table 1 for sequences of all standard and Universal primers utilized. The structure and function of the Universal reverse transcription (URT) primer is shown in FIGS. 6, 7 and 8.

All standard-design primers used were designed to be "mRNA-specific" by standard, conventional-design criteria: a) the primer pair spans a genomic DNA intron or b) the individual primer oligonucleotide traverses a cDNA exon/exon splice site. Any potential product resulting from amplification of a processed pseudogene encoded by a contaminating genomic DNA cannot be distinguished from cDNA-derived product by these standard techniques, without additional controls such as a "no-RT" control. The standard-design primers are listed in Table 1. The standard sequences were designed for the forward and reverse primers in combination to span an intron in the genomic sequence, or individual primers to span a known exon/exon splice site. "N miss"=number of bases mismatched if primer is to potentially anneal to encoding gene sequence (genomic DNA, but not pseudogene). The suffix Fup (e.g. β-Actin (Fup)) refers to the transcript-specific forward primer of the forward-Universal reverse PCR primer pair used to amplify transcripts with suspected pseudogenes. The designation URP refers to the Universal reverse primer used in the PCR of cDNA where a homologous, contaminating genomic DNA-encoded pseudogene sequence is known or suspected (e.g. β-Actin).

TABLE 1

Standard-design primer sequences used for comparison with Universal primers.

| Target | Forward primer | SEQ ID No. | Reverse Primer | MRNA product | Gene product | SEQ ID NO. |
|---|---|---|---|---|---|---|
| β-Actin (std) | ccacgaaactaccttcaactcc | 1 | tcatactcctgctgcttgctgatcc | 270 bp | 382 bp (6 miss) | 2 |
| GAPDH (std) | ggtcggagtcaacggatttggtcg | 3 | cctccgacgcctgcttcaccac | 788 bp | 3016 (4 miss) | 4 |
| 36B4 (std) | ctacttccttaagatcatccaac | 5 | tcaaagagaccaaatccca | 915 bp | None (ex/ex) | 6 |
| CYP1B1 (std) | gccactatcactgacatct | 7 | cttgcctcttgcttcttatt | 684 bp | 3716 bp | 8 |
| CYP1A1 (std) | ttccgacactcttccttagt | 9 | atggttagcccatagatggg | 368 bp | 705 bp | 10 |
| GST-M1 (std) | actttcccaatctgccctac | 11 | ttctggattgtagcagatca | 191 bp | None (ex/ex) | 12 |
| GST-P1 (std) | caccaactatgaggcgggcaa | 13 | atcagcagcaagtccagca | 159 bp | 338 bp (8 miss) | 14 |
| GST-M1 (Fup) | catgatctgctacaatccagaa | 15 | URP | 807 bp | None | NA |
| GST-P 1 (Fup) | tctccttcgctgactacaac | 16 | URP | 282 bp | None | NA |
| β-Actin (Fup) | gccatcctaaaagccacc | 17 | URP | 345 bp | None | NA |
| GAPDH (Fup) | gcacaagaggaagagagaga | 18 | URP | 211 bp | None | NA |
| 36B4 (Fup) | gacaatggcagcatctacaa | 19 | URP | 480 bp | None | NA |

NA = not applicable

Methods of extraction of RNA are well-known in the art and are described, for example, in J. Sambrook et al., "Molecular Cloning: A Laboratory Manual" (Cold Spring Harbor Laboratory Press, Cold Spring Harbor, N.Y., 1989), vol. 1, ch. 7, "Extraction, Purification, and Analysis of Messenger RNA from Eukaryotic Cells," incorporated herein by this reference. Typically, RNA isolation is performed in the presence of chaotropic agents such as guanidinium chloride or guanidinium thiocyanate, although other detergents and extraction agents can alternatively be used.

Essentially any nucleic acid sequence, in purified or non-purified form, can be utilized as the starting nucleic acid(s) for the methods of the present invention, provided it comprises the desired specific nucleic acid sequence (i.e., complementary to the cDNA synthesis primer). It is only generally preferred that a sufficient number of bases at one end of the sequence be known in sufficient detail, so that a primer can be prepared which will hybridize to one of the strands of the desired sequence. A mixture of primers (including specific or degenerated sequences) may also be employed if more than one nucleic acid sequence is the target.

It is also not necessary that the sequence to be amplified is initially present in a pure form; it may be a minor fraction of a complex mixture, or a portion of a nucleic acid sequence. Therefore, the amplification process is useful not only for producing large amounts of one specific nucleic acid sequence, but also for simultaneously amplifying more than one different specific nucleic acid sequence located on the same or different nucleic acid molecule, in a heterogeneous nucleic acid background.

This RNA-specific RT-PCR method was designed for accurate mRNA amplification, but could conceivably be adapted for other purposes. The nucleic acid(s) may be obtained from any source, for example, from plasmids such as pBR322, from cloned DNA or RNA, or from natural DNA or RNA from any source, including bacteria, yeast, fungi, viruses, organelles, and higher organisms, such as plants or animals. DNA or RNA may be extracted from blood, serum, plasma, cerebrospinal fluid, tissue material/biopsies or cells by a variety of techniques such as those described by Sambrook et al., 1989, Molecular Cloning: A laboratory Manual.

As used herein, the term "Universal RT-primer" refers to an oligonucleotide designed for reverse transcription having three components (general formula): 1) a 3' anchor region, 2) an oligo-dT midsection and 3) a specific and unique invariate sequence to be used as a target for the amplification primers in the subsequent PCR amplification reaction. The primer component will be capable of acting as a point of initiation of synthesis, typically DNA polymerization, when placed under conditions in which synthesis of a primer extension product that is complementary to a nucleic acid strand is induced, i.e., in the presence of appropriate nucleotides and a replicating agent (e.g., a DNA polymerase) under suitable conditions, which are described by Sambrook et al., 1989, Molecular Cloning: A laboratory Manual.

The PCR primers are preferably single stranded oligodeoxynucleotides. Each primer must be sufficiently long to act as an initiation point for the synthesis of extension products from template in the presence of the replicating agent. The exact lengths of the primers and the quantities used will depend on many factors, including temperature, degree of homology and other conditions. Preferably, the PCR primer length is between 15 and 25 nucleotides long with an equal distribution of purines and pyrimidines, aiming at reaching an annealing temperature between 40–70° C.

For example, the transcript-specific PCR primer typically contains between about 10 and 50 nucleotides, preferably 15–25 nucleotides. For other applications like differential display (Liang & Pardee, 1992), the oligonucleotide primer is typically, but not necessarily, shorter, e.g., 7–15 nucleotides. Such short primer molecules generally require lower hybridization temperatures to form sufficiently stable hybrid complexes with the template.

The oligonucleotide primers may be prepared using any suitable method, such as, for example, the well-known phosphotriester and phosphodiester methods, or automated embodiments thereof. One method for synthesizing oligonucleotides on a modified solid support is described in U.S. Pat. No. 4,458,066. It is also possible to use a primer that has been isolated from a biological source (such as a restriction endonuclease digest).

The primers herein are selected to be "substantially" complementary to the different strands of each specific sequence to be amplified, i.e., the primers should be sufficiently complementary to hybridize with their respective strands at a annealing temperature from 40° to 70° C. Therefore, the primer sequence need not reflect the exact sequence of the template, and can, in fact, be "degenerate." Non-complementary bases or longer sequences can be interspersed into the primer, provided that the primer sequence has sufficient complementarity with the sequence of the strand to be amplified to permit hybridization and extension, and therefore amplification.

Generally, it is not necessary to know the sequence of a target mRNA for reverse transcription, as the primer may be a poly(T) of sufficient length to hybridize with substantially all members of an entire population of mRNAs (i.e., poly $(T)_n$, wherein n is typically from about 16–26). Of course, when more sequence knowledge is available for a target RNA, the primer may be designed more specifically, which may increase the efficiency of the amplification. If a sequence-specific primer is used in the first strand cDNA synthesis, the specific target RNA may be preferentially reverse transcribed. However, the carry over of both sequence-specific RT primer and contaminating genomic DNA into the PCR reaction may, during PCR thermocycling, result in amplification of a genomic DNA-derived pseudogene, if one exists for that transcript.

Moreover, the primers may actually comprise a collection of primer sequences, such as where more than one target sequence exists. Also, if there is ambiguity in the sequence information, a number of primers should be prepared. In particular, when any of several possible nucleic acid sequences encoding a protein could be correct based on a polypeptide sequence obtained from a fragment of the protein, a collection of primers containing sequences representing most or all of the possible codon variations (utilizing codon degeneracy) can be prepared.

Reverse Transcription

The Universal RT primer anneals specifically to the mRNA to initiate reverse transcription. The Universal RT primer includes: (i) a variable 3', three-base anchor (a mixture of all possible combinations of sequences that can also prevent primer slippage) to recognize all mRNA targets and anchor the Universal RT primer to the last 3 bases of the mRNA target adjacent 5' to the polyA tail (N=all bases, V=A, C or G); (ii) a tract of 16–26 thymidine (T) residues, advantageously n=16, 17, 18, 19, 20, 21, 22, 23, 24, 25 or 26 and preferably n=21 to recognize the specific poly-A tail of the target mRNA; and (iii) 18 residues that are fixed for all RT primer transcripts, which are not complementary to mRNA target, and hence remain unbound during the reverse transcription process. The reverse transcriptase extends the 3' end of the RT primer producing a mRNA-cDNA heteroduplex. RNaseH selectively degrades the mRNA strand, leaving a cDNA that is the reverse complement of the original mRNA which now has a 18 base tag at the 5' end. This tag is not related to the original mRNA and is the same for all cDNA species. The reverse transcription process takes place at 50° C. where DNA is double stranded and therefore unavailable as a template for the RT primer, consequently the genomic DNA does not incorporate the 18 base tag (see FIG. 7).

Universal RT-Coupled PCR

During the PCR, the transcript-specific forward primer anneals to the newly synthesized cDNA. Taq DNA polymerase extends the forward primer at the 3' end resulting in double stranded DNA (both strands having the 18-base tag). The reaction is heated to 95° C. and the double-stranded DNA is denatured. The Universal reverse primer that has a sequence identical to the 18 base tag integrated during the RT step now primes the anti-sense strand (3'–5'). Only cDNA reverse transcribed with the Universal RT primer has this tag. There is no identical sequence for the Universal reverse PCR primer in human genomic DNA, therefore the reaction will not inappropriately amplify genomic DNA. The transcript-specific forward primer primes the sense strand and the specific product is amplified. Cycling continues per standard PCR kinetics (see FIG. 8).

The PCR reaction is carried out under conditions for the preparation of double-stranded cDNA from mRNA that are well-known in the art. Such techniques are described, for example, in Volume 2 of Sambrook et al., "Molecular Cloning: A Laboratory Manual", entitled "Construction and Analysis of cDNA Libraries." Typically, reverse transcriptase from avian myeloblastosis virus is used.

Detection of RT-PCR Reaction Products

The PCR can be performed in the presence of $^{35}$S-dATP, $^{32}$P-labeled deoxyribonucleoside triphosphate, such as $^{32}$P dCTP. However, it is generally preferred to use a $^{35}$S-labeled deoxyribonucleoside triphosphate for maximum resolution. Other detection methods, including nonradioactive labels, can also be used.

RT-PCR reaction products may be detected by a variety of methods such as a multi-well plate, a gel, a membrane, a solid matrix, A tube or a capillary.

Preferably, the amplification product may be subjected to agarose gel electrophoresis or polyacrylamide gel electrophoresis and stained with ethidium bromide, SYBR Green etc., to measure the density of the amplification product band. Alternatively, oligonucleotide primers or the nucleotides are conveniently labeled. Commonly employed labels include, but are not limited to, biotin, fluorescent molecules, radioactive molecules, chromogenic substrates, chemiluminescence, and the like. The methods for biotinylating nucleic acids are well known in the art, as are methods for introducing fluorescent molecules and radioactive molecules into oligonucleotides and nucleotides.

For the detection of RT-PCR reaction products, the RT or PCR primers may be attached to solid substrates such as latex beads or DNA chips. Luminex Corp., (Austin, Tex.) provides the LabMAP system which incorporates polystyrene microspheres (beads) that are internally dyed with two spectrally distinct fluorochromes. Using precise ratios of these fluorochromes, an array is created consisting of 100 different microsphere sets with specific spectral addresses with each microsphere set possessing different reactant on its surface. Microspheres are interrogated individually in a rapidly flowing fluid stream as they pass by two separate lasers in the Luminex$^{100}$ analyzer. PharmaSeq, Inc. (See U.S. Pat. No. 6,001,571) provides a multiplex assay for nucleic acids containing bead(s) conjugated to a transponder which is a radio transmitter-receiver activated for transmission of data by reception of a predetermined signal. Illumina, Inc. provides a BeadArray™ technology which combine fiber optic bundles and specially prepared beads that self-assemble into an array.

The RT or PCR primers of the present invention may also be attached to a solid support, as disclosed in U.S. Pat. No. 6,324,479. The solid support may be made from glass, plastic (e.g. polypropylene, nylon, polyester), polyacrylamide, nitrocellulose, or other materials. Generally, non-porous supports, and glass in particular, are preferred embodiments. The solid support may also be treated in such a way as to enhance the binding of oligonucleotides or to reduce non-specific binding of unwanted substances. Preferably, the glass support is treated with polylysine or silane to facilitate attachment of oligonucleotides to the slide.

Methods of immobilizing DNA on the solid support may include direct touch, micropipetting (Yershov et al., Proc. Natl. Acad. Sci. USA (1996) 93(10):4913–4918), the use of controlled electric fields to direct a given oligonucleotide to a specific spot in the array (U.S. Pat. No. 5,605,662). DNA is typically immobilized at a density of 100 to 10,000 oligonucleotides per $cm^2$ and preferably at a density of about 1000 oligonucleotides per $cm^2$. However a preferred method for attaching the nucleic acids to a surface is by printing on glass plates, as is described generally by Schena et al., (Science 270:467–470, 1995. This method is especially useful for preparing microarrays of cDNA. See also DeRisi et al., 1996, Nature Genetics 14:457–460; Shalon et al., 1996, Genome Res. 6:639–645; and Schena et al., Proc. Natl. Acad. Sci. USA, 1996, 93(20):10614–19).

An alternative to immobilizing pre-fabricated oligonucleotides onto a solid support is to synthesize oligonucleotides directly on to the surface of the support (Maskos et al., Nucl. Acids Res. 21: 2269–70, 1993; Fodor et al., Science 251: 767–73, 1991; Lipshutz et al., 1999, Nat. Genet. 21(1 Suppl):20–4). Other methods of synthesizing oligonucleotides directly on a solid support, particularly preferred methods are photolithography (see Fodor et al., Science 251: 767–73, 1991; McGall et al., Proc. Natl. Acad. Sci. (USA) 93: 13555–60, 1996), piezoelectric printing (Lipshutz et al., 1999, Nat. Genet. 21(1 Suppl):20–4) or by masking (Maskos and Southern, 1992, Nuc. Acids Res. 20:1679–1684).

The present invention also encompasses high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767–773; Pease et al., 1994, Proc. Natl. Acad. Sci. USA 91:5022–5026; Lockhart et al., 1996, Nature Biotechnol. 14:1675–80; Trulson et al., U.S. Pat. No. 5,578,832 Lockhart et al., U.S. Pat. No. 5,556,752, , Fodor et al., U.S. Pat. No. 5,510,270 and Lipshutz et al., 1999, Nat. Genet. 21(1 Suppl):20–4.).

Detection methods are well known for fluorescent, radioactive, chemiluminescent, chromogenic labels, as well as other commonly used labels. Briefly, fluorescent labels can be identified and quantitated most directly by their absorption and fluorescence emission wavelengths and intensity. A microscope/camera setup using a light source of the appropriate wave length is a convenient means for detecting fluorescent label. Radioactive labels may be visualized by standard autoradiography, phosphor image analysis or CCD detector. The microscope/camera setup may be attached to an automated data acquisition system for the automated measurement recording and subsequent processing of the fluorescence intensity information. Such automated systems are described in U.S. Pat. Nos: 5,143,854 and 6,207,960.

Source of Material for Analysis and Preparation of RNA Therefrom

The methods of the present invention can be used to analyze gene expression from any material in which genes are expressed to generate mRNA molecules having poly-A tails. Thus, the methods of the invention can be used to measure gene expression in any animal cell or tissue. In one embodiment the cells or tissues used are mammalian in origin. In a preferred embodiment the cells or tissues are human in origin.

The cells or tissues may be form any suitable source, including, for example, blood, brain, spleen, bone, liver, prostate, mammary, heart, kidney, bladder, reproductive organs, vascular, lung, testis, intestine, nose, oropharynx, muscle, pituitary, endocrine glands, lymph node and dispersed primary cells. The tissue may be an embryonic or fetal tissue. The cell population may be a few cells, or up to 100 to 1,000,000 cells or more, as desired.

The cell or tissue samples used can be of any size and form, for example, intact organs, parts of organs, biopsy samples, swabs, skin samples, hair samples, bodily fluids, histological sections or dispersed cell suspensions, can be used. The term "swab" as used herein, can apply to any sample of material obtained by contacting an implement with a bodily surface whereby the implement picks up a sample of cells. Such swabs can be obtained using absorbent pads, brushes, scrapers etc. Examples of the types of swabs that can be obtained include cervical papanicolaou smears, tonsillar samples, samples of nasal epithelium, samples from the lining the oral cavity (buccal cells), and skin swabs. Any available amount of cellular material can be used. For example, RNA can be extracted from chunks of tissue or from single cells.

Many means of collecting such materials, such as performing, dissections, biopsies, and swabs, are routinely used and are well known in the art. Methods of collecting very small samples of materials include, for example, laser-capture microdissection, and single electrode techniques such as the "patch clamp." Such techniques make it possible to obtain, and study gene expression in, specific cells of interest without contamination from other cells. Examples 3, 4, and 5 herein, demonstrate that the methods of the present invention can be successfully used to analyze gene expression using such "small-scale" samples.

RNA can be extracted from the cell or tissue sample using any methods known in the art, such as, for example, those methods described in J. Sambrook et al., "Molecular Cloning: A Laboratory Manual" (Cold Spring Harbor Laboratory Press, Cold Spring Harbor, N.Y., 1989), vol. 1, ch. 7, "Extraction, Purification, and Analysis of Messenger RNA from Eukaryotic Cells," the contents of which are hereby incorporated by reference. Typically, RNA extraction is performed in the presence of chaotropic agents such as guanidinium chloride or guanidinium thiocyanate, although other detergents and extraction agents can alternatively be used. It should be noted that RNA need not necessarily be isolated or extracted from the sample tissues or cells for use in the methods of the present invention. For example, the methods of the present invention can be used in conjunction with in-situ RT-PCR techniques.

Applications of the Universal RT-coupled PCR Methods of the Present Invention

The specific amplification of mRNA for the quantitation of gene expression is central to the understanding of a wide range of biological processes, including gene regulation, development, differentiation, senescence, oncogenesis, pathogenesis of disease and many other medically important processes. Gene expression data obtained using the Universal RT-coupled PCR methods of the present invention can be used for multiple research, clinical, forensic, and other applications. For example, in one-embodiment, Universal RT-coupled PCR can be used to detect expression of disease-associated markers, thereby facilitating diagnosis of disease. In another embodiment, the methods of the present invention can be used to obtain information about changes in gene expression over time. Gene expression data obtained using the methods of the present invention can be used to provide information on disease risk, development or presence, to monitor efficacy of drug treatment, exposure to drugs (including drugs of abuse) hormone levels, levels of neurochemicals, response to dietary factors, progression of disease, and myriad other uses. The ability to use the methods of the present invention with small tissue samples, and samples that can readily be obtained using non-invasive methods (such as buccal cell swabs) greatly facilitate the application of such methods. For example, buccal cell samples can quickly and easily be obtained from patients and used to screen for drug- or toxin-induced changes in gene expression, or to screen for markers of pre-cancerous oral lesions or viral infection.

Although the paradigms of the present invention will provide a useful adjunct to PCR in a wide variety of diagnostic or other studies, especially facilitated are studies of gene expression in essentially any mammalian cell or cell population. Although the cell may be from blood (e.g., lymphocytes, such as T or B cells), a typical source of cell or tissue RNA or nucleotides will be solid organs, such as brain, spleen, bone, heart, vascular, lung, nose, oropharynx, kidney, bladder reproductive organs, liver, pituitary, endocrine glands, lymph node, dispersed primary cells, tumor cells, skin, hair, or the like. The cell, tissue etc. may be an embryonic or fetal tissue. Thus, in the neural research area, identification of mRNAs which vary as a function of arousal state, behavior, drug treatment, and development, for example, has been hindered by both the difficulty in construction of cDNA libraries from brain tissue and in the relative spatial insensitivity of subtractive hybridization techniques. Use of the Universal RT-coupled PCR amplification method in construction of cDNA libraries from individual brain nuclei will provide for greater representation of low-abundance mRNAs from these tissues compared with their representation in whole brain cDNA libraries, and facilitate cloning of important low-abundance messages.

The materials for use in the methods of the present invention are ideally suited for preparing of kits, produced in accordance with well known procedures, and are therefore readily provided in kit form for a variety of uses. Such a kit may comprise containers, each with one or more of the various reagents (typically in concentrated form) utilized in the methods, including, for example, buffers, the appropriate nucleotide triphosphates (e.g., dATP, dCTP, dGTP and dTTP; or rATP, rCTP, rGTP and UTP) which may be labeled, such as with fluorophores or radioactive labels (e.g. fluorescein, Cy3, Cy5, rhodamin and Texas Red; or $^{32}P$, $^{33}P$, $^{35}S$, $^{3}H$, $^{125}$ and $^{14}C$ and the like), reverse transcriptase, DNA polymerase, T4 DNA ligase, the adapter and one or more primer complexes of the present invention (e.g. appropriate length poly(T) or random primers linked to a promoter reactive with the RNA polymerase). A set of instructions will also typically be included.

Figure 13:
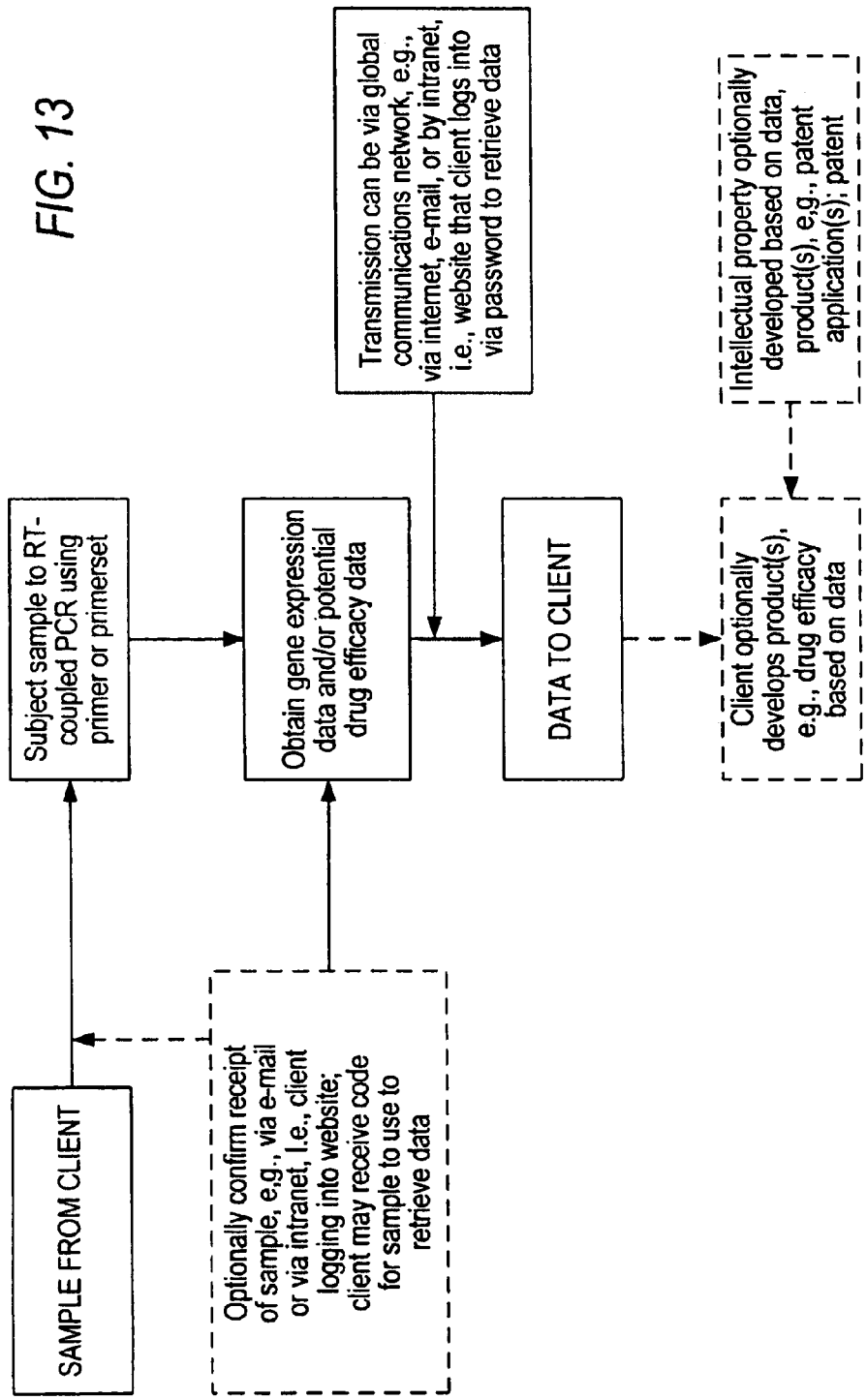
FIG. 13 shows a flow diagram illustrating the process of transmission of gene expression data and/or drug efficacy to the client via global communications such as the internet, e-mail or via intranet.

The present invention further encompasses a method of doing business comprising receiving a sample from a client, subjecting the sample to RT-coupled PCR using the primer set having the formula 3'-NVVT$_n$X-5', wherein N is equal to all base combinations, V=A, C, or G, n=16–26, advantageously n=16, 17, 18, 19, 20, 21, 22, 23, 24, 25 or 26 and preferably n=21 and X having the nucleotide sequence 5'-AAC GAG ACG ACG ACA GAC-3' (SEQ ID No. 20) and thereby generating expression data and/or drug efficacy data from the sample, and transmitting said expression data and/or drug efficacy data to said client via global communications network (see FIG. 13). Global communications networks include the internet and other information networks. For example, data can be transmitted via website posting, such as by subscription or select or secure access thereto and/or via email and/or via telephone, IR, radio or television other frequency signal, and/or via electronic signals over cable and/or satellite transmission and/or via transmission of disks, cds, computers, hard drives, or other apparatus containing the information in electronic form, and/or transmission of written forms of the information, e.g., via facsimile transmission and the like. Thus, the invention comprehends a user performing according to the invention and transmitting information therefrom; for instance, to one or more parties who then further utilize some or all of the data or information, e.g., in the manufacture of products, such as therapeutics, antisense oligos, probes, assays, diagnostic tests etc. The invention also comprehends disks, cds, computers, or other apparatus or means for storing or receiving or transmitting data or information containing information from methods and/or use of methods of the invention. Thus, the invention comprehends a method for transmitting information comprising performing a method as discussed herein and transmitting a result thereof.

Further still, the invention comprehends methods of doing business comprising performing some or all of a herein method or use of a herein composition, and communicating or transmitting or divulging a result or the results thereof, advantageously in exchange for compensation, e.g., a fee. Advantageously the communicating, transmitting or divulging is via electronic means, e.g., via internet or email, or by any other transmission means herein discussed. Thus, the invention comprehends methods of doing business involving the compositions (primers or primer sets) and methods of the invention.

The present invention may also be further described by the following numbered paragraphs:

1. A Universal reverse transcription (RT) primer that binds to the mRNA of an animal species, comprising
   a) a 3'anchor sequence which binds to coding nucleotides in the mRNA of the animal species,
   b) a poly T midsection which binds to poly A tails in the mRNA of the animal species,
   c) a 5' tag whose sequence does not occur in the genome of the animal species.

2. A primer set comprising the Universal reverse transcription (RT) primer of paragraph 1.

3. A primer set comprising: a Universal reverse transcription (RT) primer that binds to the mRNA of an animal species and comprises
   a) a 3'anchor sequence which binds to coding nucleotides in the mRNA of the animal species,
   b) a poly T midsection which binds to poly A tails in the mRNA of the animal species,
   c) a 5' tag whose sequence does not occur in the genome of the animal species, at least one transcript-specific forward PCR primer, and a reverse PCR primer having the sequence of the 5' tag of the Universal reverse transcription (RT) primer.

4. A Universal reverse transcription (RT) primer having the formula 3'-NVVT$_n$X-5', wherein N is equal to all base combinations, V=A, C, or G, n=16–26 and X having the nucleotide sequence 5'-AAC GAG ACG ACG ACA GAC-3' (SEQ ID No. 20).

5. The Universal reverse transcription (RT) primer according to paragraph 1, wherein n=21.

6. A primer set having the formula 3'-NVVT$_n$X-5', wherein N is equal to all base combinations, V=A, C, or G, n=16–26, X having the nucleotide sequence 5'-AAC GAG ACG ACG ACA GAC-3' (SEQ ID No. 20) a forward primer and at least one reverse primer identical to X; or comprising at least a Universal RT primer of any one of paragraphs 1–4.

7. The primer set according to paragraph 6, wherein n=21.

8. A method of selectively amplifying mRNA wherein genomic DNA amplification is avoided comprising:

reverse transcribing a mRNA template using a primer set having the formula of paragraph 6 or 7 wherein X remains unbound to said mRNA template but integrated into each cDNA molecule synthesized, thereby 5' tagging the mRNA-derived cDNA sequences comprising X, thereby allowing for selective amplification of mRNA in subsequent PCR reactions.

9. A method for the amplification of multiple different transcripts from tissue-derived RNA sample comprising:

reverse transcribing a mRNA template using a primer set having the formula of paragraph 6 or 7 wherein X is specific for all transcript-derived cDNA sequences, thereby allowing for subsequent PCR amplification of multiple different transcripts.

10. A method for constructing a cDNA library from a population of mRNA molecules in a sample, wherein the primer set according to paragraph 6 or 7 allows for selective amplification of a plurality of mRNAs in the sample wherein genomic DNA amplification is avoided.

11. A method for selectively amplifying mRNA in a cell population comprising steps of:

reverse transcribing a mRNA template using a primer set having the formula of paragraph 6 or 7 wherein X remains unbound to said mRNA template but integrated into each cDNA molecule synthesized, thereby 5' tagging the mRNA-derived cDNA sequences comprising X, thereby selectively allowing for the amplification of mRNA in a subsequent PCR reaction.

12. A method according to any of paragraphs 8–11, wherein the source of nucleic acid is selected from the group consisting of blood, serum, plasma, cerebrospinal fluid, urine, tissue samples, biopsies, saliva, swabs, cytological specimens, and buccul mucosa.

13. A method according to paragraph 12, wherein the tissue sample is selected from the group consisting of brain, spleen, bone, heart, vascular, lung, kidney, liver, intestine, muscle, blood, pituitary, endocrine glands, lymph node and dispersed primary cells.

14. A method according to paragraph 12, wherein the tissue sample or source of nucleic acid is comprised by a cell population said cell population being characterized may be single cell, or up to 100 to 1,000,000 cells or more as desired.

15. A kit suitable for selectively amplifying mRNA wherein genomic DNA amplification is avoided in a sample, said kit comprising:

a) said primer set of paragraph 6 or 7; and
b) reagents suitable for the selective amplification of mRNA in said sample.

16. A method for obtaining and/or generating gene expression data comprising subjecting a sample to RT-coupled PCR using the primer set having the formula of paragraph 6 or 7, and thereby obtaining and/or generating gene expression data.

17. A method for obtaining and/or generating gene expression data using the primer set having the formula of paragraph 6 or 7 and an automated data acquisition system, and thereby obtaining and/or generating gene expression data.

18. A method of generating gene expression data comprising:

receiving a sample from a client,
subjecting said sample to RT-coupled PCR using the primer set of paragraph 3 or 4 and thereby generating gene expression data from said sample, and transmitting said gene expression data to said client.

19. A method for obtaining and/or generating drug efficacy data comprising subjecting a sample to RT-coupled PCR using the primer set having the formula of paragraph 6 or 7, and thereby obtaining and/or generating drug efficacy data.

20. A method for obtaining and/or generating drug efficacy data using the primer set having the formula of paragraph 6 or 7 and an automated data acquisition system, and thereby obtaining and/or generating drug efficacy data.

21. A method of generating drug efficacy data comprising:

receiving a sample from a client,
subjecting said sample to RT-coupled PCR using the primer set of paragraph 6 or 7 and thereby generating drug efficacy data from said sample, and transmitting said drug efficacy data to said client.

22. A method for obtaining and/or generating gene expression data and drug efficacy data comprising subjecting a sample to RT-coupled PCR using the primer set having the formula of paragraph 6 or 7, and thereby obtaining and/or generating gene expression data and drug efficacy data.

23. A method for obtaining and/or generating gene expression data and drug efficacy data using the primer set having the formula of paragraph 6 or 7 and an automated data acquisition system, and thereby obtaining and/or generating gene expression data and drug efficacy data.

24. A method of generating gene expression and drug efficacy data comprising:

receiving a sample from a client,
subjecting said sample to RT-coupled PCR using the primer set of paragraph 6 or 7 and thereby generating gene expression data and drug efficacy data from said sample, and transmitting said gene expression data and drug efficacy data to said client.

25. A method of providing data comprising: transmitting data electronically, wherein the data is from RT-coupled PCR using the primer set of paragraph 6 and 7.

26. The method of paragraph 25 wherein the data is transmitted by e-mail.

27. The method of paragraph 25 wherein the data is transmitted by posting on a network.

28. The method of paragraph 27 wherein the network is a global communications network (worldwide web, internet).

29. The method of paragraph 27 wherein the data is transmitted by posting on an intranet.

30. The method of paragraph 25 wherein the data is transmitted via a transmission medium.

31. A method of providing data comprising:

recording data electronically, wherein the data is from RT-coupled PCR using the primer set of paragraph 6 and 7.

32. The method of paragraph 31 wherein the data is recorded via a recording medium.

The invention will now be further described by the following non-limiting Examples, given by way of illustration.

EXAMPLES

Example 1

A. DNase Treatment of Total RNA Isolated From Lung Tissue

Materials and Methods

1) RNA isolation: Total RNA was extracted from approximately 100 mg of frozen human lung tissue using a thiocyanate guanidinium-based method (TRI Reagent protocol, Molecular Research Center Inc., Cincinnati, Ohio). Lung tissue was fractioned and pulverized using liquid nitrogen to minimize RNA degradation. The frozen pulverized lung tissue was then immediately immersed in TRI Reagent and RNA isolation was performed according to manufacturer protocol. RNA was also isolated from MCF7 breast cancer cells harvested from a 25 cm$^2$ culture flask grown to confluence, according to the Tri Reagent protocol. Human lung total RNA was purchased as a standard, from Clontech (Palo Alto, Calif.), which had been isolated by the manufacturer using a guanidinium-based chemical method.

2) DNA isolation: DNA was isolated from viably frozen peripheral blood mononuclear cells using a Puregene® DNA Isolation Kit (Gentra Systems, Minneapolis, Minn.). The isolation was performed according to the manufacturer's protocol (which includes an RNase treatment) from 1–2 million cultured cells. To ensure complete degradation of any contaminating RNA, an additional RNase treatment was performed as follows: Puregene ® kit-isolated DNA was incubated at 65° C. for 1 hr, the sample was then cooled to 37° C. and 1.5 µl of RNaseA (Gentra Systems) was added per 50 µl of DNA and the sample was incubated at 37° C. for a minimum of 1 hour.

3) DNase Treatment: DNase treatment of total RNA and subsequent RT was performed according to the method of Huang et al (BioTechniques Vol. 20, No 6,1012–20, 1996) which is herein incorporated by reference. Briefly, 2.5 µg of total RNA was added to 4 µl of 5×first strand buffer (Gibco/BRL Life Technologies, Gathersburg, Md.), 2 µl of 0.1M DTT and 8 µl of DNTP mix (10 uM/base Roche, Branchburg, N.J.). Water was added to a total volume of 16.5 µl. Samples were mixed gently and incubated at 42° C. for 2 minutes and 2.5 µl of RNase-free DNase I (Boehringer Mannheim, Indianapolis, Ind.) was added and the samples were incubated at 37° C. for 30 minutes. The RNase-free DNase enzyme was denatured at 75° C. for 10 minutes and then cooled to 4° C. RT was then performed as noted below.

4) Reverse Transcription: Standard oligo dT-RT was performed using 2.5 µg of total RNA using Superscript II Reverse Transcriptase (Life Technologies, Gathersburg, Md.) as follows. For non-DNase-treated samples: the RNA template was added to 1 µl of RT primer (0.5 µg/µl Oligo (dT) or 100 uM Universal reverse transcriptase primer), 1 µl of DNTP mix (10 uM each) and DNase/RNase-free water to a volume of 12 µl. The solution was incubated at 65° C. for 5 minutes and then cooled to 4° C. A master mix containing 4 µl of 5×first strand buffer (Gibco/BRL Life Technologies, Gathersburg, Md.), 2 µl 0.1mM DTT and 1 µl DNase/Rnase-free H$_2$O per RT sample was prepared, and added to each sample. The sample was then incubated at 42° C. for two minutes. SuperScript II Reverse Transcriptase (Gibco/BRL Life Technologies, Gathersburg, Md.) was added (1 µl) and the samples were incubated at 42° C. for 50 minutes followed by 70° C. for 15 minutes. For DNase-treated samples: Following DNase treatment, each sample received 1 µl of Oligo (dT) RT primer and was incubated at 70° C. for ten minutes and then quickly cooled to 4° C. Samples were incubated at 42° C. for two minutes and SuperScript II Reverse Transcriptase was added (1 µl) and the samples were incubated at 42° C. for 50 minutes followed by 70° C. for 15 minutes. Two units of RNaseH (Life Technologies, Gathersburg, Md.) was added to each tube and followed by a 20-minute incubation at 37° C.

For samples intended for assay using the Universal primers rather than the standard primers, the Universal reverse transcription primer was added to designated total RNA samples in place of oligo-DT in identical concentration (0.5 µg/µl). The Universal RT primer has the formula 3'-NV-VT$_n$X-5', wherein N is equal to all base combinations, V=A, C, or G, n=16–26, X having the nucleotide sequence 5'-AAC GAG ACG ACG ACA GAC-3'(SEQ ID No. 20).

5) Polymerase Chain Reaction: PCR was performed using either a Perkin Elmer Biosystems 9700 block thermocycler or a Roche Molecular Biochemicals LightCycler® System, as per figure captions. Block PCR reactions were performed using Taq DNA polymerase supplemented with Platinum Taq Antibody or Platinum Taq DNA polymerase (enzyme and antibody pre-mixed) from Gibco/BRL Life Technologies (Gathersburg, Md.). PCR reactions included 1 µl of template (cDNA or genomic DNA) according to the manufacturer protocol, for 35–40 cycles. LightCycler® PCR reactions were performed (40 cycles) using a Qiagen (Valencia, Calif.) Hot Start™ DNA Polymerase kit with the following modifications. The reaction volume was scaled down to 20 µl. Each reaction consisted of 4 µl of 5×PCR buffer from a Qiagen (Valencia, Calif.) One Step RT-PCR Kit (in place of the 10×buffer in the Hot Start Kit.), 0.8 µl dNTP mix (10 mM of each), 0.6 µl of Hot Start enzyme, 1.0 µl of 1×SYBR Green I dye (Molecular Probes, Eugene, Oreg.), 13.6 µl 0f DNase/RNase-free H$_2$O and 1 µl of template (cDNA).

6) PCR Primers: The standard-design primers for GAPDH, CYP1B1 and CYP1A1, β-Actin (Trummer et al. Journal of Hematotherapy & Stem Cell Research 9:275–284.2000) and the GST-M1 standard-design reverse primer (Lacave et al. British Journal of Cancer 77(5) 694–702. 1998) are listed in Table 1.

Results and Conclusion

Figure 1:
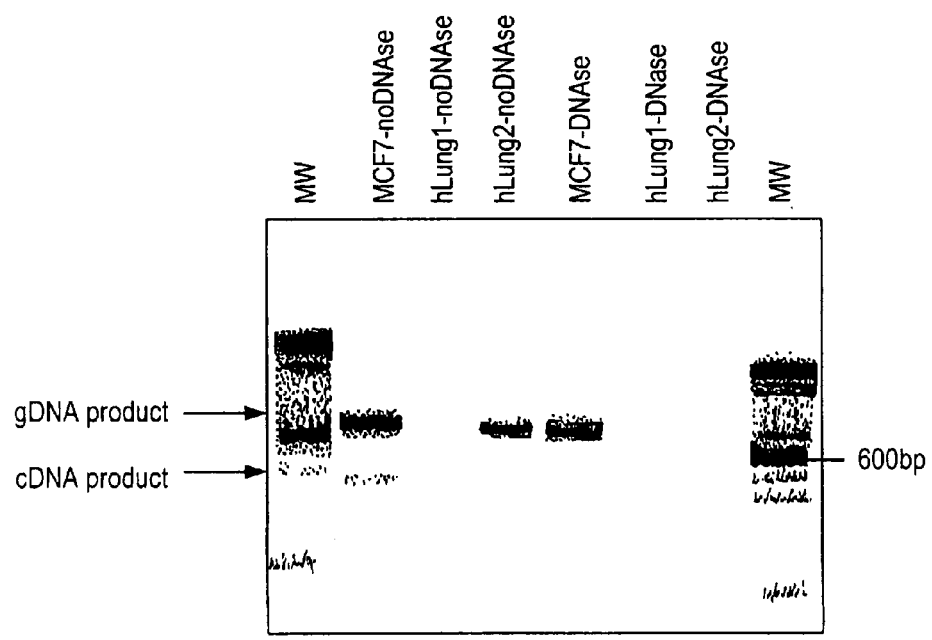
FIG. 1 shows an agarose gel illustrating the inefficacy of DNase treatment of human lung "RNA" samples amplified for CYP1A1 mRNA by standard RT-PCR. Lanes 1 and 8=molecular weight markers (MW). Lane 12=MCF7 total RNA; lane 3=human lung RNA1; lane 4=human lung RNA2. DNase treatment of the total "RNA" samples prior to RT for: lane 5=MCF7 RNA; lane 6=human lung RNA1; and lane 7=human lung RNA2. All "RNA" samples were extracted by standard guanidinium thiocyanate-based methods. Larger molecular weight bands reveal genomic DNA material in these "RNA" samples, incompletely obliterated by aggressive DNAse treatment. There is no known pseudogene encoded in genomic DNA for CYP1A1.

As described in FIG. 1, lane 1 (RNA extract from MCF7 breast cancer cells) shows both a genomic DNA-sized product (710 bp) and a mRNA/cDNA-sized product (370 bp) using standard-design CYP1A1 RT and PCR primers. Lane 2 (human lung RNA1) shows only the mRNA/cDNA-sized product and lane 3 (human lung RNA2) shows only the genomic DNA-sized product. After DNase treatment, the genomic DNA-sized remains present in both the MCF7 (lane 1a) and the human lung RNA2 (lane 3a). Also the mRNA/cDNA-sized product is significantly reduced in the human lung RNA1 sample (lane 2a) compared to lane 2 where no DNase was added.

In this example, different standard-design CYP1A1 cDNA-PCR primers were being tested. For CYP1A1 there is no known pseudogene discovered to-date. Therefore, PCR primers that amplify both RNA and genomic DNA are a result of the application of standard and appropriate design rules for this transcript, that in this case yielded a suboptimal PCR primer design, amplifying the genomic DNA product as well as the cDNA product. These CYP1A1 PCR primers produce both genomic DNA and cDNA product in a clearly size-distinguishable manner (genomic DNA=710 bp, cDNA=370 bp). This combination of features allows the effects of DNase treatment on both RNA and genomic DNA to be monitored simultaneously in the "RNA" extract. For all samples tested there was a decrease or complete loss of mRNA/cDNA signal with DNase treatment. Also a genomic DNA signal remained in the samples following DNase treatment. (see FIG. 9B). Therefore, DNase treatment failed in its primary purpose to eliminate any contaminating genomic DNA from the human lung RNA extracts, and also resulted in a loss of target RNA. Clearly, contaminating genomic DNA is common in standard "RNA" extracts, and DNase is insufficient to extinguish that signal without compromising mRNA/cDNA-derived signal.

These results emphasize the need for an improved method for the specific detection of mRNA which is consistently free of contaminating genomic DNA.

Figure 2:
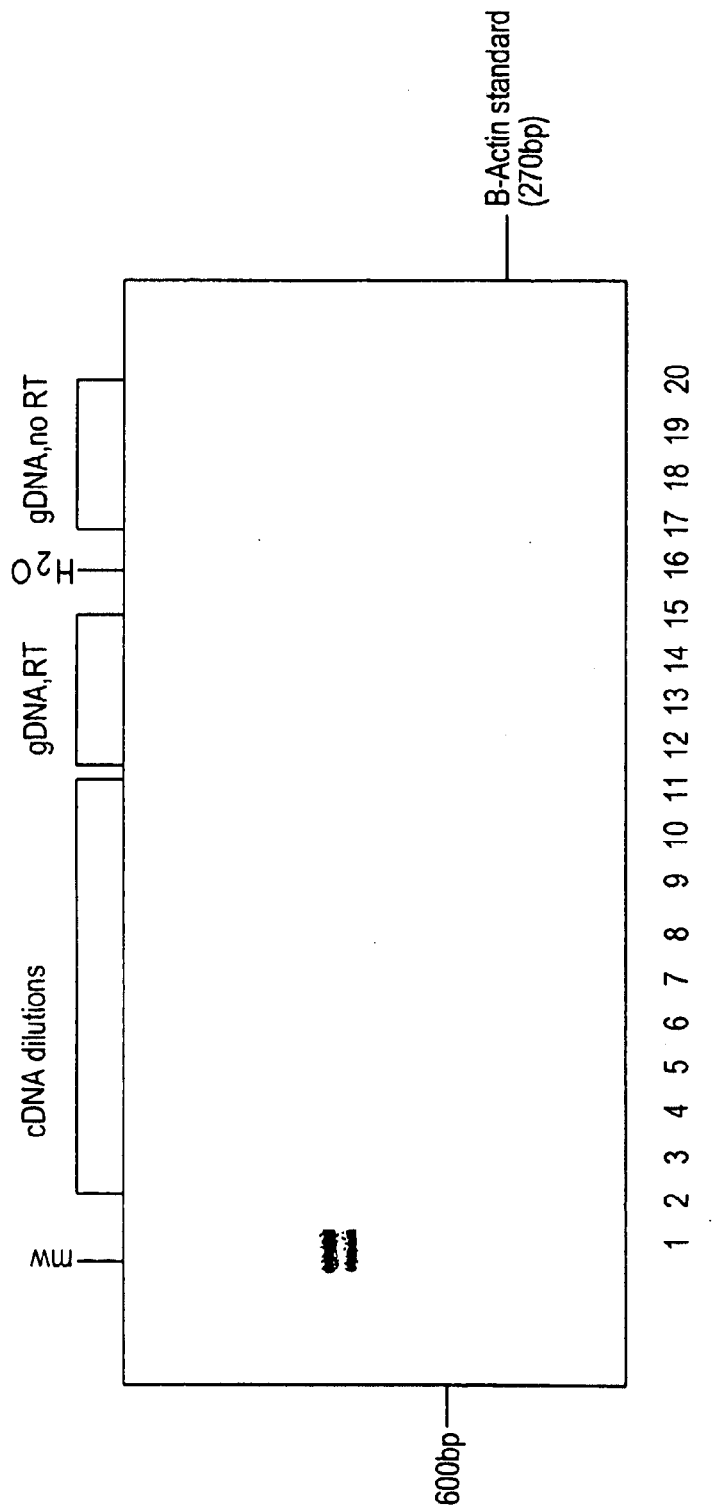
FIG. 2 shows an agarose gel illustrating β-actin pseudogene-encoding genomic DNA in the "RNA" sample amplified by standard odT-RT, and standard-design PCR primers. Lane 1=MW marker, lanes 2–11=cDNA dilutions, lanes 12–15=genomic DNA, lane 16-H$_2$O and lanes 17–21=genomic DNA (no RT). The cDNA-sized product is apparent in the genomic DNA lanes. Residual cDNA-sized product remained in the genomic DNA lanes, even after DNAse treatment (see also FIG. 9B).

B. Amplification of Housekeeper Genes β-actin, 36B4 and GAPDH Using Standard-design Primers As shown in FIG. 2, there is a mRNA/cDNA-sized band of 270 bp for all samples and conditions, including genomic DNA, using the standard-design β-actin primer set, including for those samples that did not undergo RT. The no RT samples serve as a control to show that any possible trace contaminants of RNA in the genomic DNA cannot be contributing to the product signal in the absence of an RT step. The mRNA/cDNA-sized band in genomic DNA samples is due to amplification of a processed pseudogene and is not an RNA-derived product. These results show that there is indeed a problem discriminating between mRNA and contaminating genomic DNA using standard β-actin primers.

Figure 3:
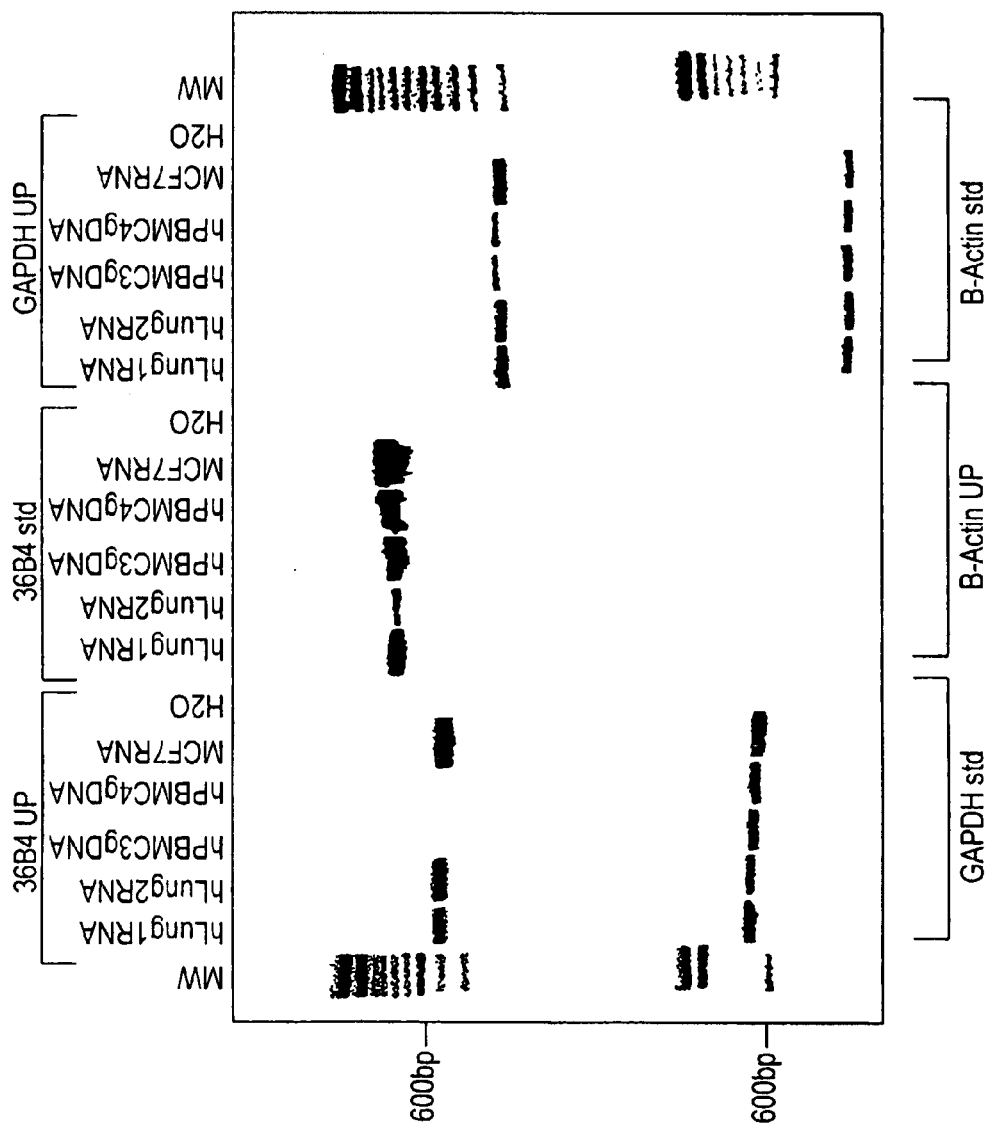
FIG. 3 shows an agarose gel illustrating genomic DNA-encoded pseudogene contamination during amplification of housekeeper genes 36B4 and GAPDH. Each panel of 6 lanes represents a different primer set applied to the same samples. Lanes 1, 2, 5=cDNA, lanes 3, 4=genomic DNA (RNase-treated, 4 hrs at 37° C.), lane 6=water (no cDNA) blank. Panel A: 36B4 Universal RT-PCR primers; Panel B: 36B4 standard odT-RT and standard-design PCR primers; Panel C: GAPDH Universal RT-PCR primers; Panel D: GAPDH standard odT-RT and standard-design primers; Panel E: β-actin Universal RT-PCR primers; Panel F: β-actin standard odT-RT and standard-design RT-PCR primers.

RNA transcript specificity of the Universal RT-coupled PCR method has also been achieved for other pseudogene-encoded reference "housekeeper" transcripts in common use, including GAPDH and 36B4 (FIG. 3). The gel shows RNA-specific RT-PCR for 36B4 via the Universal Primer (UP) strategy, GAPDH (UP) where confounding band is visually size-distinguishable, and β-actin (BAUP). Comparison with identical-size signal derived from human peripheral blood monocyte-isolated genomic DNA (Gentra Puregene® kit, with an RNAse step) highlights this specificity. These reference housekeeper transcripts, as well as nonpseudogene-confounded transcripts, have been reproducibly amplified using this Universal RT-coupled PCR method from extraordinarily small samples such as cytologically-collected human cells, and in laser-capture microdissected samples, both numbering 10–100 cells.

Example 2

A. Quantitative Real-Time RT-PCR and PCR Analysis Using β-actin Standard Primers Total RNA was isolated from normal human lung tissues and lung tumors using a thiocyanate guanidinium-based method (Tri®-Reagent protocol, Molecular Research Center, Inc., Cincinnati, Ohio) as discussed in Example 1. Standard reverse transcription RT-PCR was performed as in Example 1 except that 1.0 μl of 1×SYBR Green I dye (Molecular Probes, Inc., Eugene, Oreg.) was added to the PCR reaction.

Results

TABLE 2

Quantitative real-time RT-PCR of isolated total RNA using standard β-actin primers:
RT-PCR versus PCR only (data derived from Figures 4A and 4B)

| Sample | meanCRO RT-PCR (FIG. 4A) | meanCRO PCR (FIG. 4B) | Difference |
|---|---|---|---|
| 16t | 12.31 | 17.17 | 4.83 |
| 58t | 15.96 | 21.02 | 5.06 |
| 58nt | 17.00 | 20.66 | 3.66 |
| 2782t | 16.31 | 15.99 | 0.32[1] |
| 2782nt | 21.78[2] | 24.14 | 2.36 |
| LDt | 14.53 | 20.41 | 5.88 |
| LDnt | 18.79 | 25.05 | 6.24 |
| H₂O | nd | nd | na |

The Roche LightCycler® real-time quantitative PCR system was used to quantitate product, using the crossover (CRO) midpoint of the log-linear plot of fluorescence (double-stranded PCR product, SYBER® Green intercalator dye) versus PCR cycle number. The presence of PCR product in the no-RT conditions by standard oligo dT RT-PCR suggests a significant contribution of genomic DNA-derived pseudogene for samples 16T, 58T and 58NT (see FIGS. 4A and 4B). The difference between the RT-PR and PCR-only conditions is proportional to the signal contribution from RNA transcript.

Figure 4A:
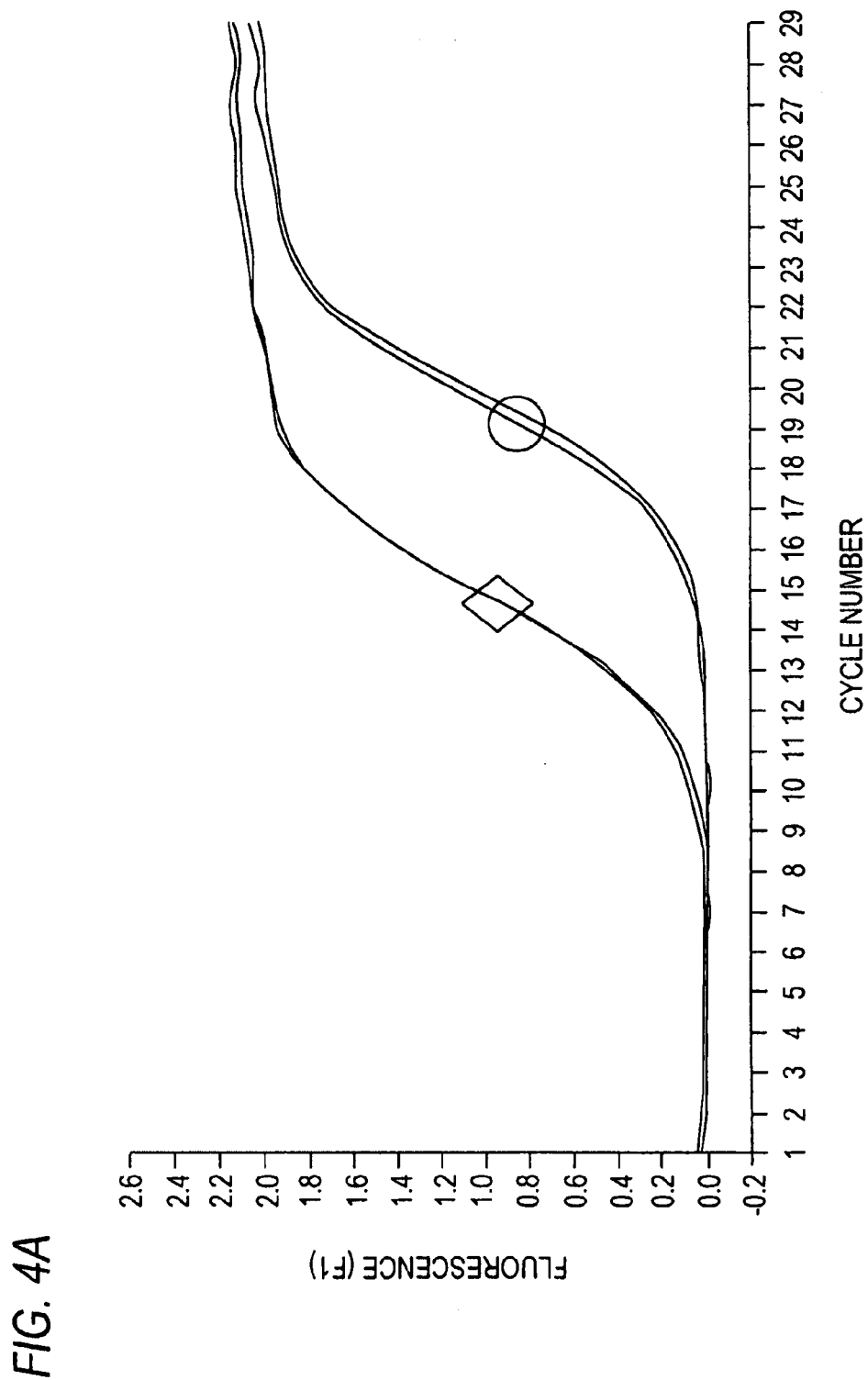
FIGS. 4A and 4B show graphic LightCycler® data analysis illustrating quantitative real-time RT-PCR of isolated total "RNA" from human lung tissue using standard odT-RT and standard-design β-actin PCR primers, yielding both RNA and pseudogene-derived product, versus quantitative real-time PCR-only (no reverse transcription, RT) of isolated total "RNA" from human lung tissue using standard-design β-actin PCR primers, yielding pseudogene-derived product only. The y-axis shows fluorescence (F1) and the x-axis PCR cycle number. The difference in these two conditions (RT-PCR versus PCR only) represents product derived from mRNA.
Figure 4B:
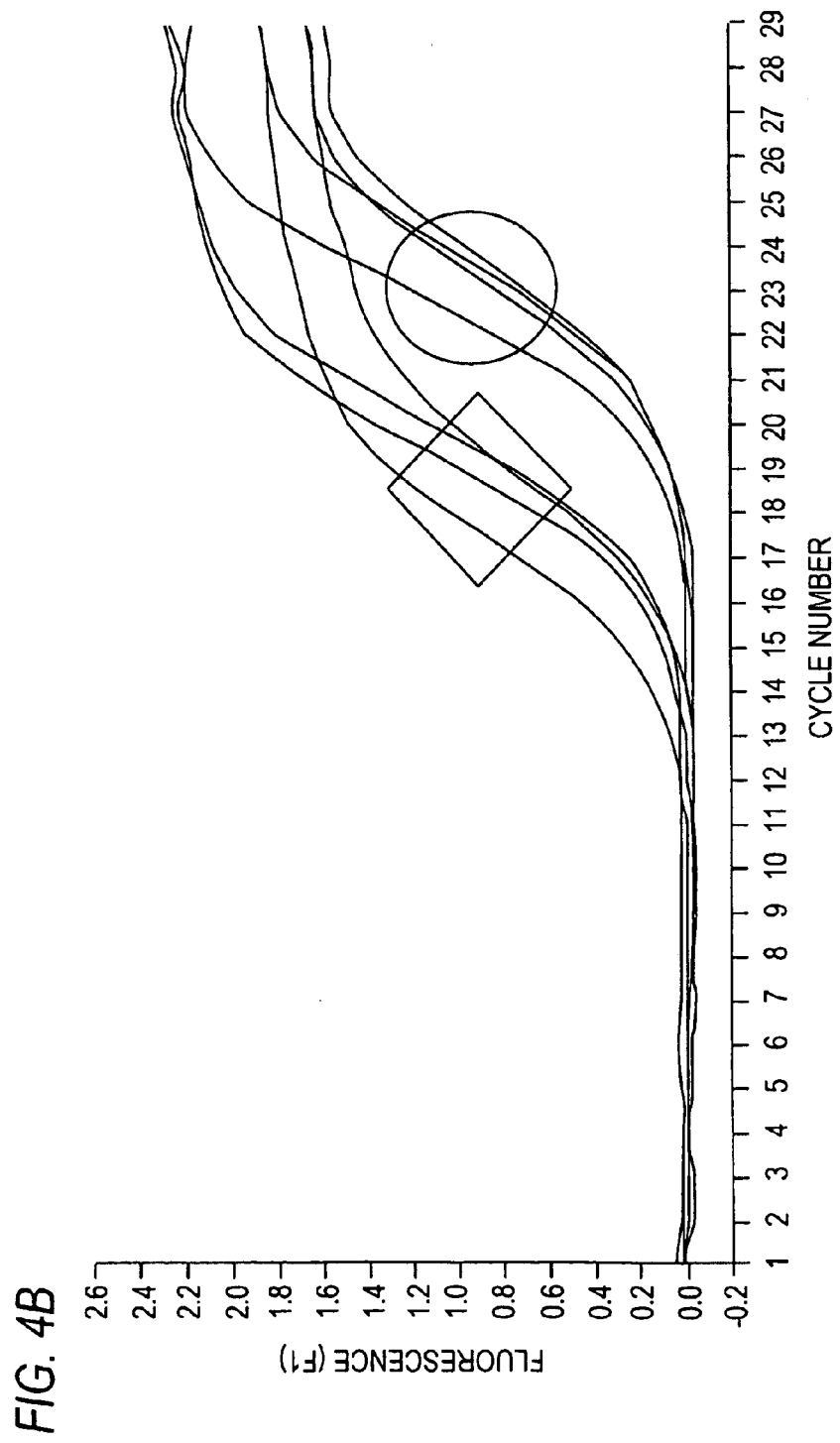

The lower the CRO number the more the original starting template. For all samples tested in FIGS. 4A and 4B, samples were run with both a standard oligo dT-RT step and a standard-design β-actin PCR primer set. FIG. 4A represents LightCycler® quantitative comparative data for sample 16T, and FIG. 4B for samples 58T and 58NT. The PCR-only control detects pseudogene contribution to the signal. Table 2 displays mean CRO data for samples derived from the tumor-nontumor sets from several individuals, performed in duplicate. The average cycle difference for PCR vs RT-PCR is 4, implying that there is an average $2^4$ more RT-PCR product, or on average 16-fold more RNA than genomic DNA in guanidinium-extracted "total RNA" preps. There is inter-sample variability in the RNA/DNA ratio, from 1:1 to 64:1, in these total RNA samples. This intersample variability poses difficulties for any attempt to arithmetically or otherwise nonexperimentally "correct" for genomic DNA-derived signal after non-RNA-specific RT-PCR.

It has thus been demonstrated by real-time quantitative RT-PCR (FIGS. 4A 4B, and Table 2) that genomic DNA encoding pseudogene can make up 1–50% of traditionally isolated "RNA" macroscopic tissue extracts.

For all the samples tested above, mRNA-derived PCR product for the transcript CYP1B1 has been identified by electrophoresis and direct sequencing (data not shown). Since CYP1B1 has no known pseudogene, it is concluded that all "RNA" samples tested herein do indeed have intact mRNA, and therefore contribute some mRNA-derived signal to the total β-actin signal.

Figure 9A:
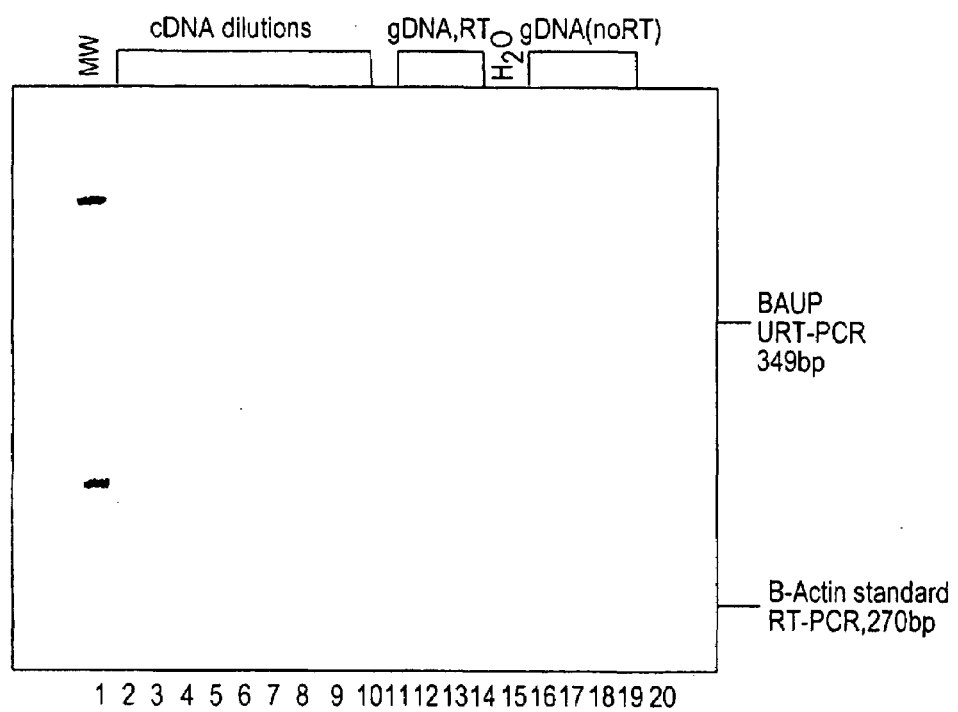
FIG. 9A shows an agarose gel comparing the specificity of standard oligo dT-RT and standard-design β-actin PCR primers, versus Universal RNA-specific RT-PCR primer set with no DNase added. Lane 1=MW marker, lanes 2–11=cDNA, lanes 12–15=genomic DNA (RT), lane 16=H$_2$O, lanes 17–20=genomic DNA (no RT).
Figure 9B:
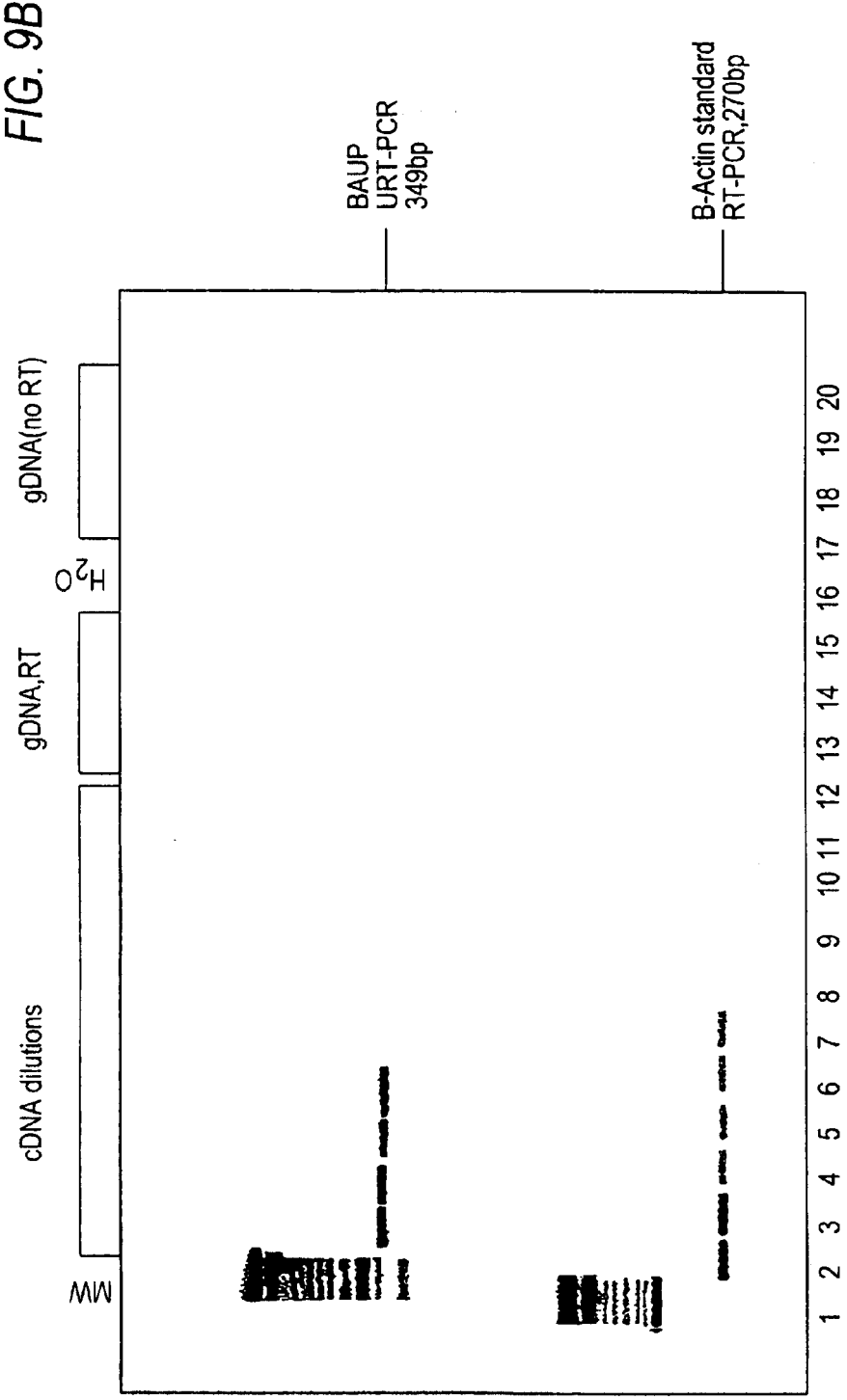
FIG. 9B shows an agarose gel showing the specificity of the Universal RT-PCR primer set for β actin (BAUP), compared to standard oligo dT-RT and standard-design β-actin primers for mRNA detection when the "RNA" sample is treated with an aggressive DNase protocol before reverse transcription. There remains residual genomic DNA-derived product after DNAse treatment, confounding the standard approach. Lane 1=MW marker, lanes 2–11=cDNA, lanes 12–15=genomic DNA (RT), lane 16=H$_2$O, lanes 17–20=genomic DNA (no RT).

B. Table 3: Quantitative Real-time RT-PCR, Comparing Universal RT Primers to Oligo dT Reverse Transcription Primers, Identical Standard-design PCR Primers FIGS. 3, 9A and 9B show the specificity of the Universal RT primer (e.g. BAUP) compared to β-actin standard primers for mRNA detection and illustrates that the Universal primer set (BAUP) does not show a mRNA/cDNA-sized band for the samples containing genomic DNA; only the cDNA lane is positive. In contrast, the standard β-actin primer set shows mRNA/cDNA-sized product in all the lanes. The mRNA/cDNA-sized band in the genomic DNA samples is a result of amplification of a processed pseudogene and is not amplified by the Universal primer system.

Therefore, the Universal primer set (BAUP) are specific for mRNA and consequently do not amplify the pseudogene.

TABLE 3

RT Efficiency, Universal RT versus oligo dT

| Sample | meanCRO CYP1B1 (FIG. 10A) | meanCRO GST-T1 (FIG. 10B) |
| --- | --- | --- |
| ES 102-NT (URT) | 26.99 | 24.13 |
| ES 102-NT (oligo dT) | 26.00 | 23.17 |
| EP-T (URT) | 27.25 | 25.10 |
| EP-T (oligo dT) | 25.77 | 22.77 |
| H$_2$O | nd | nd | nd = not detectable

Figure 10A:
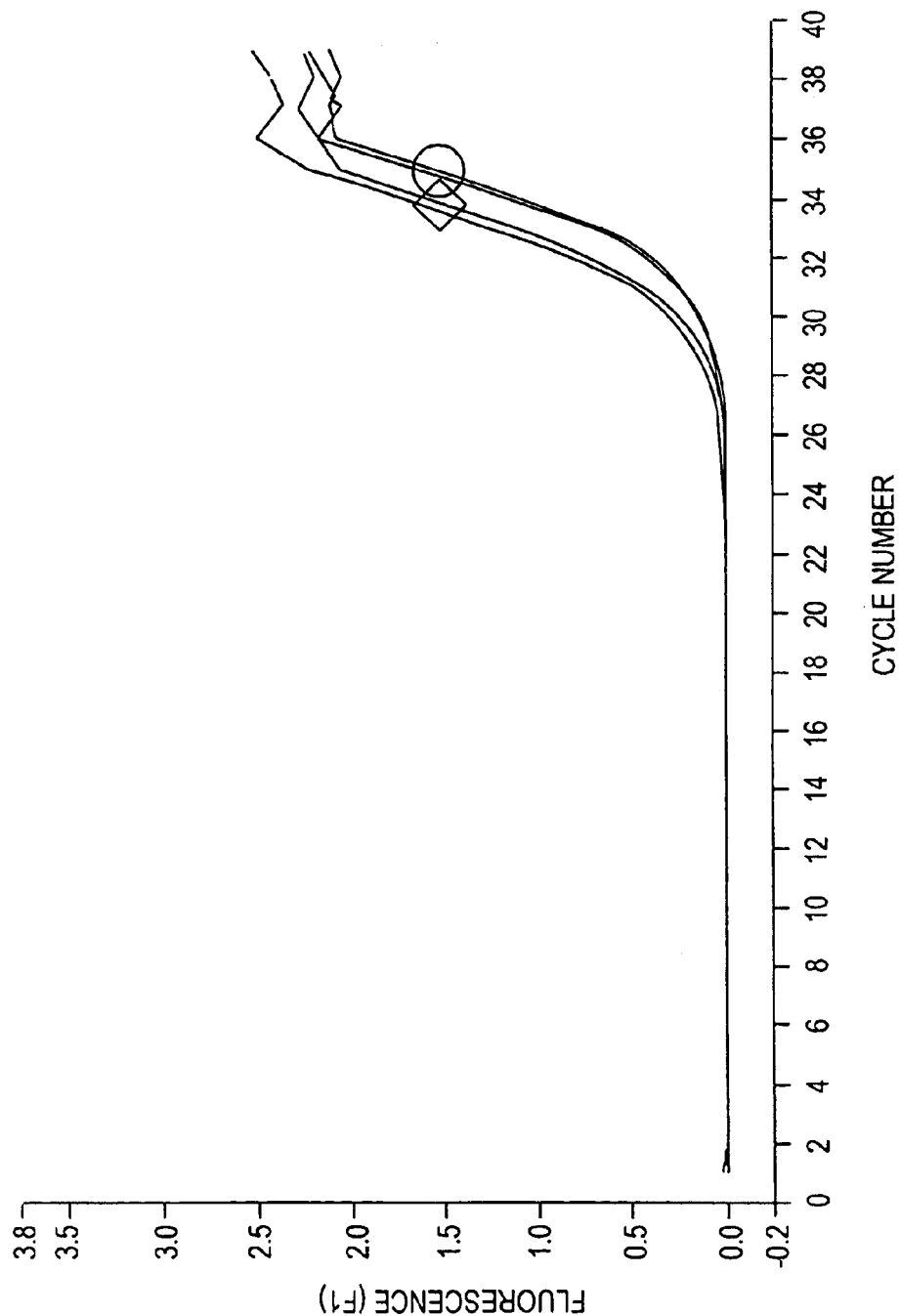
FIGS. 10A and 10B shows graphic LightCycler® quantitative RT-PCR data analysis of RT efficiency, for non-pseudogene-confounded transcripts, comparing Universal RT primer vs. oligo dT-RT primer, but identical standard-design PCR primers for 10A) CYP1B1 and 10B) GST-T1. The y-axis shows fluorescence (F1) and the x-axis PCR cycle number.
Figure 10B:
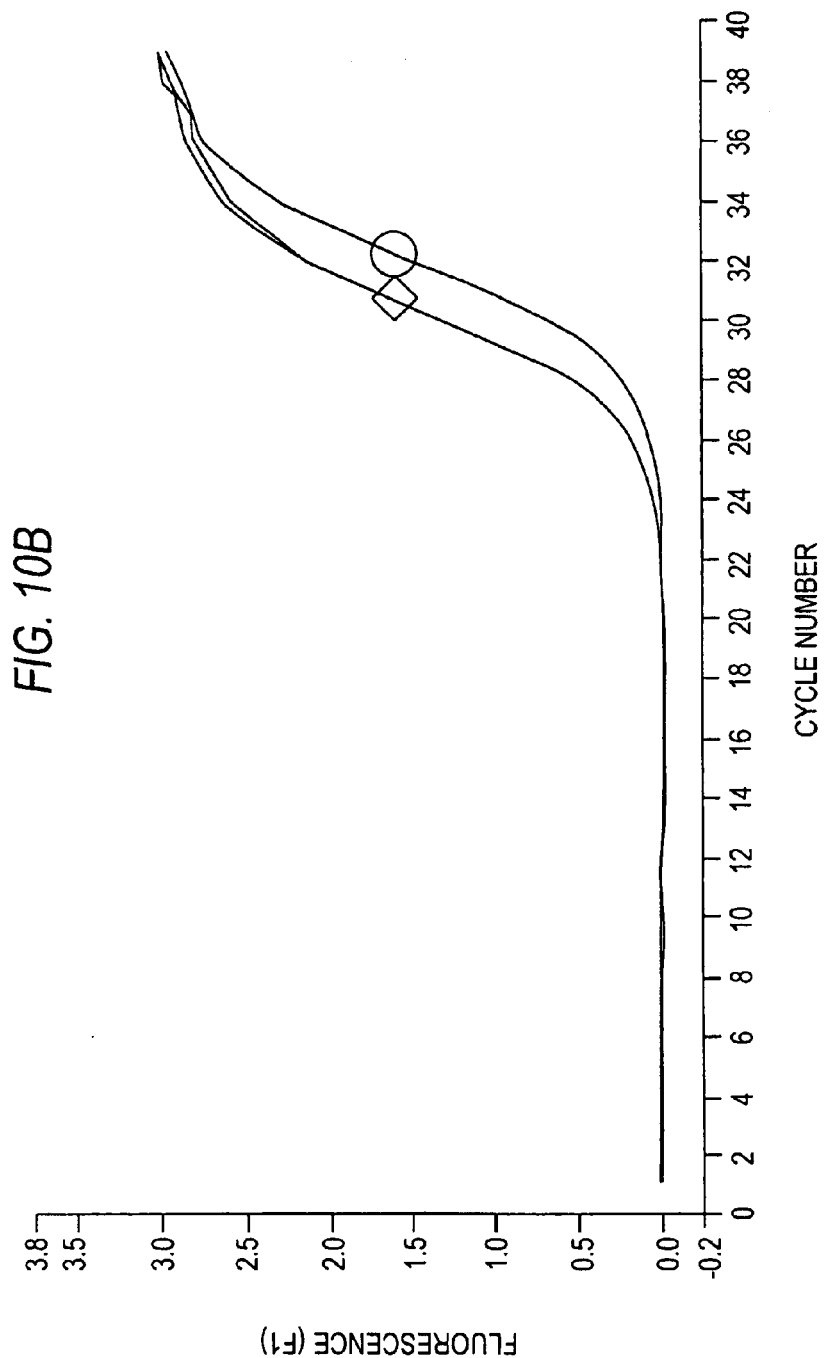

The Universal RT primers of the present invention were tested against standard oligo-dT-RT primers to determine the reverse transcription efficiency (see FIGS. 10A, 10B). In the initial tests for CYP1B1 mRNA RT-PCR (a non-pseudogene-encoded transcript), the CRO difference, and therefore the PCR cycles to reach a predetermined fluorescence threshold (double-stranded product concentration), averaged 1.21 cycles greater for Universal RT-PCR than for oligo dT-RT-PCR for these two representative human lung extracts EP-T and ES102NT. This represents an approximately two-fold RT efficiency advantage to oligo dT-RT under the conditions tested (see FIG. 10A). For GST-T1 (another non-pseudogene-encoded transcript), the URT-PCR versus oligo dT-RT-PCR difference was 1.65 cycles, representing, at maximum, an approximate three-fold efficiency advantage to oligo dT-RT under the conditions tested (see FIG. 10B). Subsequent testing on additional samples has yielded no difference in RT-PCR efficiency between the two techniques.

The Universal RT primer has been devised so that when it is combined with the coupled-design PCR primers, it yields a PCR product (e.g. BAUP) that is specifically derived from mRNA even when contaminating genomic DNA is present in the "RNA" sample, and is detectable with equivalent sensitivity. This new system is applicable to all transcripts, both those encoded by, as well as those not encoded by the genomic DNA pseudogene sequence. Thus, a 1 µg sample of total RNA can be reverse transcribed for use in multiple (e.g. 50) reactions similar to oligo dT-based RT, each PCR reaction designed to detect a different RNA sequence. This efficiency of design preserves precious mRNA from scarce human tissue sources.

GST-M1 is a member of the glutathione S-transferase family and is one of the most studied genes in assessing risk for human carcinogenesis (Cantlay et al.). FIG. 11 shows the specificity of the GST-M1 Universal RT primer compared to GST-M1 standard primers for mRNA detection. The gel illustrates that the Universal primers for GST-M1 amplify a mRNA/cDNA-sized product only for the cDNA lanes. Standard oligo dT-primed RT combined with standard-design PCR primers yield a 191 bp signal from peripheral blood mononuclear cell genomic DNA samples treated with RNase (lanes 3–7) that is identical in size to that expected from mRNA/cDNA-derived signal. Human lung tissue "RNA" extracts not undergoing RT yield an identical-sized product. Contaminating genomic DNA-encoded pseudogene sequence can account for this cDNA-sized signal, confounding the assessment of gene expression. Search of the HGP yields multiple compatible responsible sequence in the human genome. The Universal RT-PCR primer set used on the same samples avoids this false positive signal, as there is no amplification in the genomic samples. Again, the standard GST-M1 primers (designed to be mRNA specific-spans the intron) show amplification of mRNA/cDNA-sized product for cDNA, genomic DNA and RNA that has not been reverse transcribed. Therefore, the Universal primer set (BAUP) are specific for mRNA and consequently do not amplify the pseudogene.

GST-P1 is a member of the glutathione S-transferase family, and also a highly-studied gene in assessing risk for human carcinogenesis. FIG. 12 shows the specificity of the GST-P1 Universal primer compared to the GST-P1 standard primers for mRNA detection. The gel illustrates that the Universal primer GST-P1 shows amplification of a mRNA/cDNA-sized product only in the cDNA lanes as above. Standard oligo dT-primed RT combined with standard-design PCR primers yield a 159 bp signal from peripheral blood mononuclear cell genomic DNA samples treated with RNase (lanes 11–16) that is identical in size to that expected from mRNA/cDNA-derived signal. There is also a larger, presumably genomic DNA-derived signal that is not pseudogene sequence, for this standard primer set. Human lung tissue "RNA" extracts not undergoing RT yield an identical-sized product if standard PCR primers are used. Contaminating genomic DNA-encoded pseudogene sequence can account for this cDNA-sized signal, confounding the assessment of gene expression. Search of the HGP yields multiple compatible responsible sequences in the human genome. The Universal RT-PCR primer set used on the same samples avoids this false positive signal, as there is no mRNA/cDNA-sized amplification product in the genomic DNA nor non-reverse-transcribed RNA. Therefore, the Universal primer sets are specific for mRNA and consequently do not amplify the pseudogene. The standard GST-P1 primers (designed to be mRNA-specific by spanning an intron) show amplification of mRNA/cDNA-sized product for cDNA, for genomic DNA, and for RNA that has not been reverse transcribed. Additionally, there is a band at 336 bp in many samples, which is the appropriate size for the gene (exon plus intron) product, implying amplification of contaminating genomic DNA. The standard GST-P1 mRNA primers were originally designed to avoid amplifying the gene product. There is an 8-base mismatch for the gene (exon plus intron) sequence at the 5' end of the forward primer, yet there is still genomic DNA amplification. This illustrates how difficult it can be to design primers that rely on only a few mismatches for specificity.

The Universal RT-coupled PCR method of the present invention has been shown to successfully amplify mRNA transcripts for β-actin (FIGS. 3, 9A and 9B), GST-M1 (see FIG. 11), GAPDH (FIG. 3), 36B4 (FIG. 3) and GST-P1 (See FIG. 12) without co-amplification of contaminating genomic DNA pseudogene sequences.

CONCLUSION

The present invention relates to a Universal RT-coupled PCR method that specifically amplifies mRNA in the presence of contaminating genomic DNA. DNase treatment is not necessary, nor is any other treatment that sacrifices RNA yield for a DNA-free RNA isolate. Specifically-designed Universal RT and reverse PCR primers are simply utilized using standard RT-PCR protocols. The Universal RT primer, like oligo (dT), is designed to initiate the synthesis of cDNA from all mRNA transcripts present in the tissue sample and if as in the case of most transcripts, there is no genomic DNA-encoded pseudogene, then the usual and standard transcript-specific PCR primers already in use for these cDNA transcripts by traditional PCR will suffice. In this situation, the Universal RT primer acts to prime all mRNA transcripts at the same time, similar to the oligo-dT-RT method. Where there is a known or suspected genomic DNA pseudogene, the PCR can take advantage of the 18-base tag inserted uniquely into the reverse-transcribed sequence at the time of Universal RT, and employs a transcript-specific forward PCR primer paired with Universal Reverse PCR primer, to avoid amplifying genomic DNA-derived pseudogene sequence. Therefore, the system requires minimal adaptation from current RT-PCR.

This method is particularly valuable for determining gene expression in RNA isolates from small precious clinical human samples. For such samples, any method that results in a loss of RNA, such as DNase treatment or specific mRNA isolation procedures, should be avoided if possible. Additionally, a Universal RT followed by transcript-specific PCR, as opposed to transcript-specific RT, is also the most efficient use of precious RNA samples, as all mRNA species are reverse transcribed in one step from one "RNA" extract.

Example 3

Universal RT-Coupled PCR Methods for the Analysis of Gene Expression in Small Amounts of Human Lung Tissue As mentioned above, in certain situations it is desirable to measure gene expression in samples consisting of a small number of cells, or even a individual cells. Examples of such situations include analysis of gene expression of cells within microscopic tumor foci located within an otherwise normal tissue, and the analysis of gene expression of specific subtypes of neurons within a particular brain region. Similarly, there are often situations in which, through circumstance, only small amounts of tissue are available for analysis, such as if only limited amounts of tissue can obtained from a patient in a biopsy or swab, or when analysis of gene expression in forensic samples is required. In such situations, only limited amounts of material are available from which RNA can be extracted, used in RT reactions for the generation of cDNA, and analyzed by PCR. This presents certain constraints on the processing of the sample as mentioned above, and means that not all RT, PCR or RT-PCR protocols can be used in conjunction with small amounts of starting material. In the present example, it is illustrated that the novel Universal RT-Coupled PCR methods of the present invention can successfully be used to detect and quantify gene expression in small amounts of human lung tissue obtained using laser-capture micro-dissection (LCM), further highlighting the usefulness of these methods.

Figure 14:
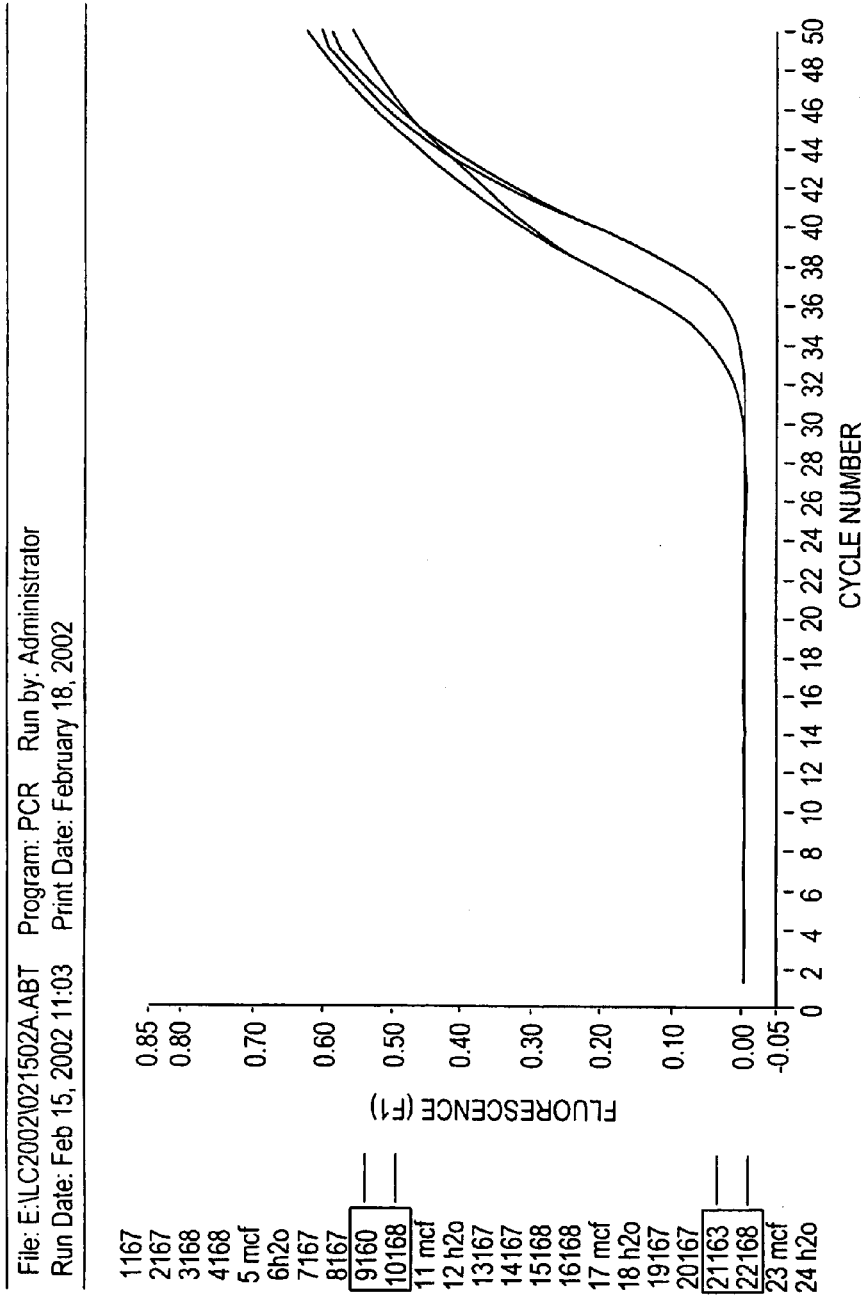
FIG. 14 shows plots of fluorescence versus PCR cycle number obtained using a Roche LightCycler®system and Universal RT-coupled real-time quantitative PCR, for GSTT1 expression (left curves) and GAPDH (right curves) in human lung samples subjected to by laser capture microdissection (LCM). The lines on the graph correspond to increasing fluorescence with PCR cycle number, in a typical LightCycler® real-time quantitative PCR display.
Figure 15:
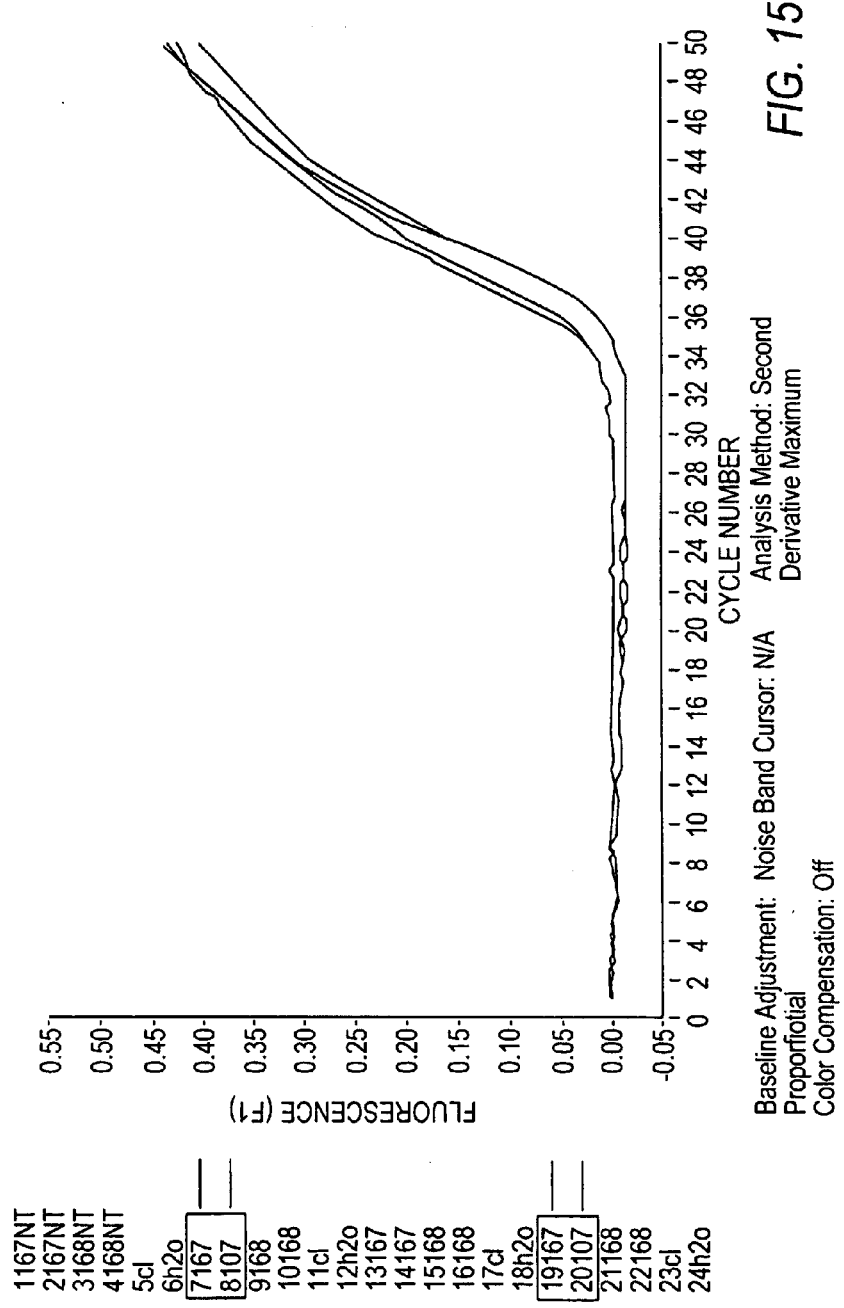
FIG. 15 shows plots of fluorescence versus PCR cycle number obtained using a Roche LightCycler® system and real-time quantitative Universal RT-coupled PCR, for GSTP1, NQ01 and GPX expression in human lung samples collected by LCM. The lines on the graph correspond to increasing fluorescence with PCR cycle number, in a typical LightCycler® real-time quantitative PCR display.

Samples were obtained using 30 laser capture pulses (approximately 5 cells per pulse) of non-malignant lung tissue from two human subjects, using standard laser capture microdissection (LCM) techniques. LCM is a standard technique used in the art to isolate small amounts of tissue. The Arcturus PixCell® Microdissection System was used, according to manufacturers instructions. RNA was extracted from these samples using standard non-phenol-containing filter immobilization methods, adapted for small samples (RNeasy®, Qiagen protocol, omitting any DNase step). In all PCR reactions, the Universal reverse primer (SEQ ID No. 20) was used. Transcript-specific forward PCR primers were sued for each gene expression analysis. Different forward primers were used for each gene whose expression was analyzed. The genes studied were GSTT1, GSTP1, NQO1, and GPX. In addition, expression of the "housekeeper" gene GAPDH was analyzed to provide a reference against which the levels of expression of the above genes could be normalized. The expression of each of the above genes was analyzed using Universal RT-coupled PCR in combination with the Roche LightCycler® real-time quantitative PCR system, essentially as described in Example 2. The LightCycler® system was used to quantitate product, using the crossover (CRO) midpoint of the log-linear plot of fluorescence (double-stranded PCR product, SYBER® Green intercalator dye) versus PCR cycle number. A lower CRO number indicates a higher level of starting template, and therefore a higher level of gene expression. FIG. 14 shows plots of fluorescence versus PCR cycle number obtained for GSTT1 on the rightwards curves, and GAPDH on the leftwards curves. FIG. 15 shows plots of fluorescence versus PCR cycle number obtained for NQO1 on the rightwards curves, and GAPDH on the leftwards curves. Table 4 provides an example of the process by which the expression of the particular gene of interest is "scaled" relative to the expression of the housekeeping gene used as the internal reference. The data shown in table 4 comes from a study in which the expression of GSTT1 and the housekeeping gene 36B4 were analyzed in samples from seven patients. It is the scaling of the expression of each gene of interest against the expression of a housekeeper reference, that makes it possible to quantitatively compare the expression of the genes of interest between patients and between different samples taken from the same patient.

Table 4: Specific Target (GSTT1) Quantitative Expression as Scaled to Internal Reference An example of scaling target transcript (GSTT1) cross over point (CRO) to reference housekeeper transcript 36B4 CRO, by using the difference or the ratio of the values in seven subjects. Values represent triplicate successful trails of RNA-specific quantitative real-time RT-PCR of laser capture microdissected non-malignant human lung material from these individuals. Subject 187 is a low GSTT1 expresser (high GSTT1 CRO when compare with reference transcript 36B4 CRO). As an example of application, these scaled values could be numerically correlated to these individual's plasma nicotine, cotinine or estradiol levels, or to categorical smoking status, dietary factors or the presence of lung disease, using multivariate models.

TABLE 4

GSTT1 Expression as Scaled to Internal Reference

| Subject | GSTT1-36B4 CRO difference | GSTT1/36B4 CRO ratio |
|---|---|---|
| 179 | 4.76 | 1.15 |
| 180 | 3.24 | 1.091 |
| 185 | −1.06 | 0.97 |
| 186 | 5.45 | 1.156 |
| 187 | 8.94 | 1.39 |
| 189 | −1.9 | 0.956 |
| 190 | 3.86 | 1.119 |

It has thus been demonstrated that the Universal RT-coupled PCR methods of the present invention, can successfully be used to obtain quantitative data on gene expression from very small amounts of human tissue. The methods of this invention can therefore be used to study, for example, a) changes in expression of specific genes in a patient in response to exposure to drugs (e.g. nicotine & cotinine), b) changes in expression of specific genes in response to changes in hormone levels, c) changes in expression of specific genes in response to dietary factors d) expression of genetic markers associated with disease (such as markers of pre-cancerous lesions or markers expressed by virally infected cells).

Example 4

Universal RT-Coupled PCR Methods for the Analysis of Gene Expression in From Small Amounts of Tissue Obtained From Swabs As described above, its is desirable to study and analyze gene expression in tissue samples consisting of a small number of cells. In example 3, it was shown that small tissue samples obtained using LCM, can be used to generate quantitative data on gene expression. In the present example, it is shown that the small number of cells typically obtained in cytological samples obtained using swabs, can also be used to generate quantitative data on gene expression. The term "swab" as used herein, can apply to any sample of material obtained by contacting an implement with a bodily surface whereby the implement picks up a sample of cells. Such swabs can be obtained using absorbent pads, brushes, scrapers etc. Examples of the types of samples that can be obtained include cervical pap smears, tonsillar samples, samples of nasal epithelium cells, samples from the lining the oral cavity (buccal cells), and skin swabs. In the present example, the tissue samples used were human buccal mucosal cells obtained using a cytological "brush" device, identical to that used for obtaining cervical cytological samples.

Another desirable use of RT-PCR described above, is its use to detect changes in gene expression in a patient over-time, for example to analyze the response of a patient to a drug, or to diagnose a disease. In the present example, it is shown that the small quantity of human buccal mucosal cells obtained, can be used to detect changes in gene expression over time induced by the smoking of cigarettes.

Figure 16:
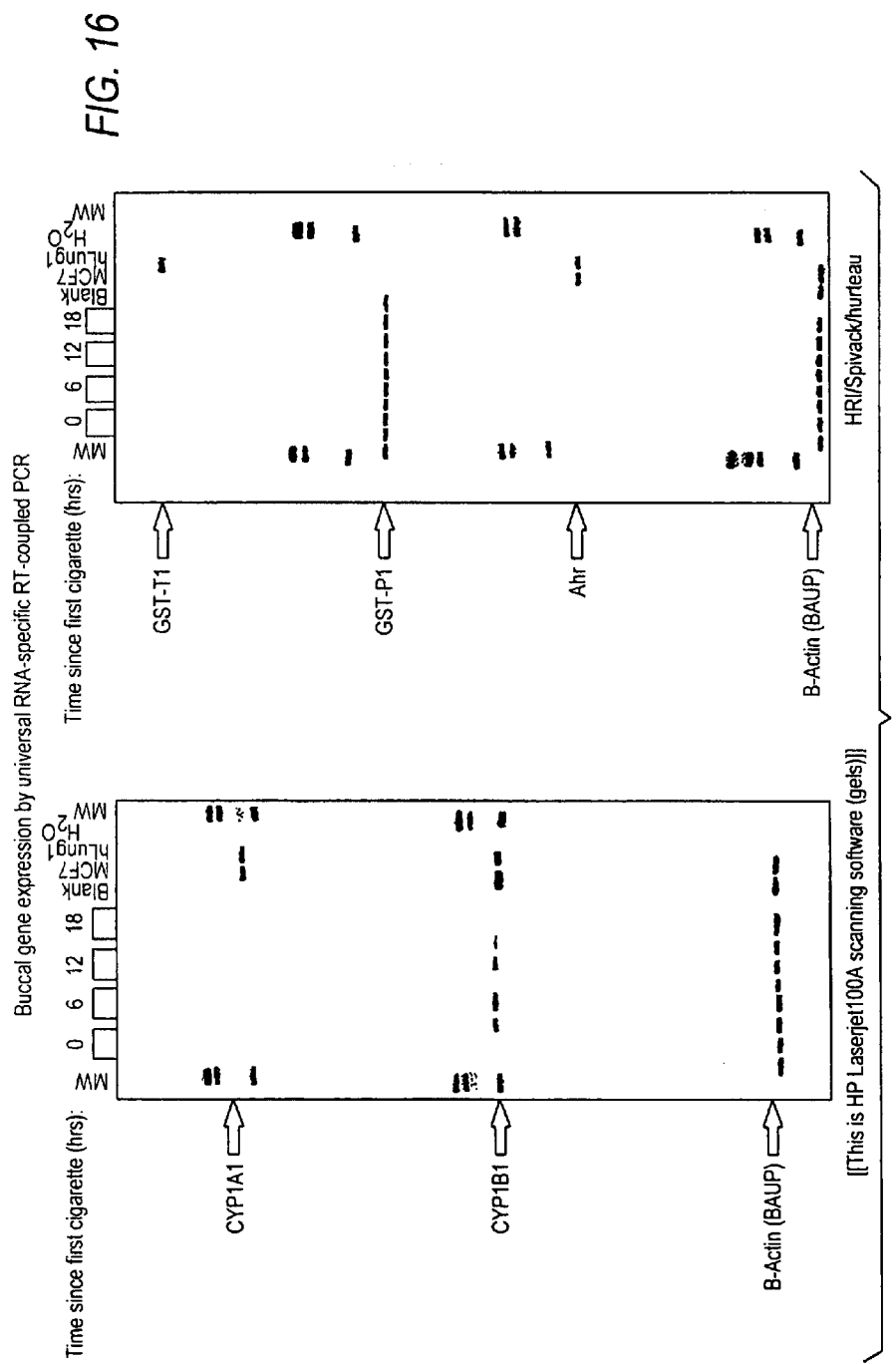
FIG. 16 A shows an agarose gel with CYP1A, CYP1B and β-actin PCR products generated using small cytologic samples and Universal RT-coupled PCR. Part B shows an agarose gel illustrating expression of GST-T1, GST-P1, Ahr, and β-actin, also determined using Universal RT-coupled PCR. The samples used were buccal swabs from a single patient, and were obtained before (0 hours) and 6, 12 and 18 hours after the patient smoked 4 cigarettes. Gene expression in human MCF7 breast cancer cells and human hLung1 cells as controls is also shown. For parts A and B, lane 1=MW marker, lanes 2–9=patient-derived buccal cell DNA, lane 10=blank, lane 11=MCF7 cells DNA, lane 12=hLung1 cell DNA, lane 13=H$_2$O, and lane 14=MW marker.

Buccal swab samples were obtained from a single subject before (0 hours) and 6, 12 and 18 hours after the onset of smoking of 4 cigarettes. The subject was a previously non-smoking, normal human subject. MCF7 breast cancer cells and hLung1 lung cell samples, were also harvested for use as controls. Samples were processed for RNA extraction, and standard or Universal RT-coupled PCR was performed essentially as described in the previous examples. RNA extraction was performed using a non phenol, solid filter immobilization technique, using the RNeasy® kit (Qiagen) in identical fashion to the LCM specimens described above. The RNA from about an estimated 100–300 buccal cells was analyzed per RT-PCR reaction. Universal RT-coupled PCR was performed using a Perkin Elmer Biosystems 9700 block thermocycler (qualitative RT-PCR) or a Roche Molecular Biochemicals LightCycler® System (quantitative RT-PCR), as in Example 1, using RNA extraction and RT-PCR reaction conditions identical to those for the laser capture microdissected material, and virtually identical to those for extracts from macroscopic specimens. FIG. 16 (parts A and B) shows agarose gels on which PCR products have been electrophoretically separated. It can be seen that expression of CYP1B1 changes as a function of time after onset of smoking. Pre-smoking, no CYP1B1 PCR product is detectable, but expression is clearly seen 6 hours after the onset and smoking, and declines thereafter. The specificity of this effect is evidenced by the fact that expression levels of CYPA1, GST-T1, GST-P1 and Ahr, are unaffected. Similarly, it can be see from the β-Actin controls, that these effects were not a result of differences in amount of starting material between samples, as expression levels of β-actin were similar across samples.

Figure 17:
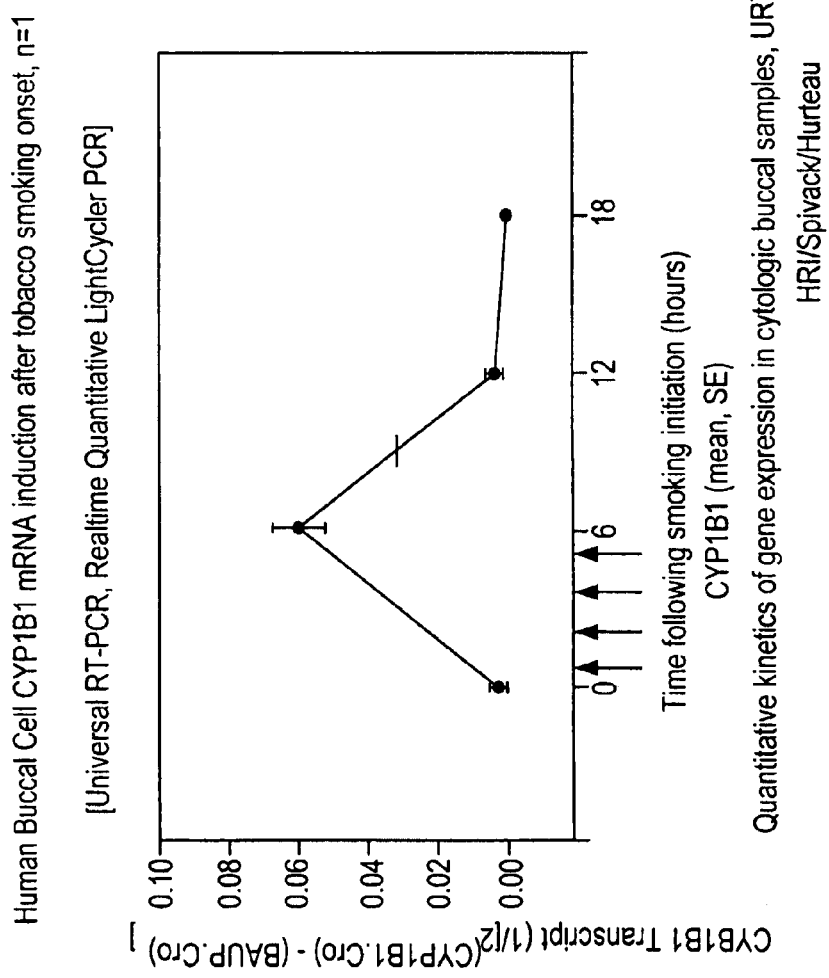
FIG. 17 Kinetics of induction of the phase I enzyme CYP1B1 in human buccal mucosal cells exposed in situ, and collected at pre=0, 6, 12, and 18 hours after the onset of smoking of 4 cigarettes (arrows) within the first 6 hours, via RNA-specific real-time quantitative RT-PCR. The subject (n=1) was a previously non-smoking, normal human subject. Induction in these cytologically brushed cells is suggested to approximate the gene induction kinetics of other smoke-exposed lung epithelial cells of smokers. Target gene CRO (CYP1B1) is scaled to the reference housekeeper gene (β-actin, BAUP) by Universal RNA-specific RT-PCR, as above.

The same samples were also analyzed using the Roche LightCycler® real-time quantitative PCR system, essentially as in Example 3. FIG. 17 shows the results of this analysis where the CRO for CYP1B1 has been scaled to that of the reference gene, β-actin.

These real-time quantitative Universal RT-coupled PCR results thus confirm that temporal changes in gene expression can be obtained from small tissue samples obtained from human subjects or patients, and that these results are truly quantitative.

Example 5

Demonstration That Universal RT-Coupled PCR Using Small Tissue Samples is RNA Specific As described above, a major advantage of Universal RT-Coupled PCR, is that it specifically detects expressed mRNA, while avoiding amplification of genomic pseudogenes. It is demonstrated above that this selectivity is indeed achieved in "large" tissue samples. In the present Example, it is demonstrated that specific detection of expressed mRNAs, can also be achieved when very small amounts of tissue are used.

Figure 18:
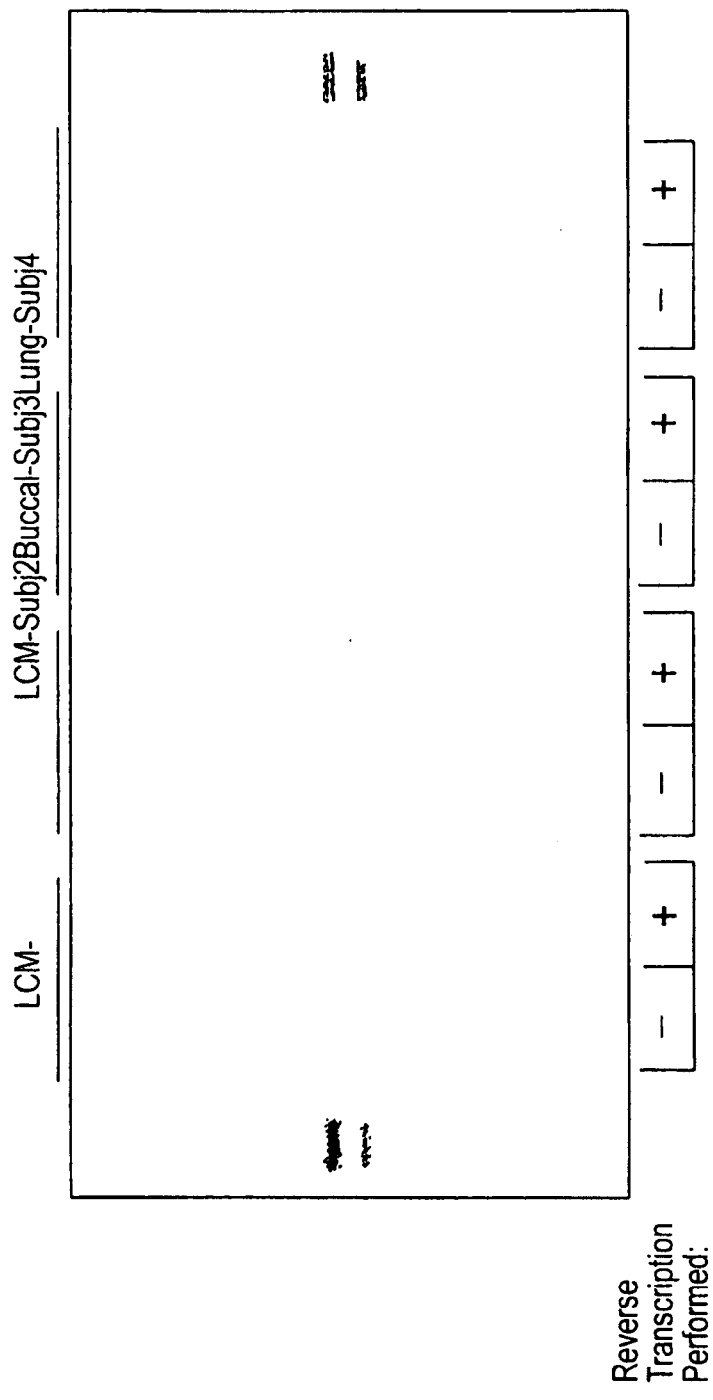
FIG. 18 shows PCR products generated using Universal RT-coupled PCR. Tissue was obtained by laser-capture microdissected (LCM), or obtained from buccal swabs, as indicated. Also shown are results from lung tissue obtained. Expression of the 36B4 housekeeping gene is shown. For each sample, reactions were performed with and without RT to assess the mRNA specificity of the PCR. Lane 1=MW marker, lanes 2–5=LCM samples from subject 1, lanes 6–9=LCM samples from subject 2, lanes 10–13=buccal cell samples, lanes 14–17=human lung cell DNA and lane 18=MW marker.

Two laser capture micro-dissected human lung specimens, one specimen from a buccal swab, and one sample of standard homogenized human lung. After RNA isolation, Universal RT-coupled PCR was performed (either in the presence or absence of RT) using a Perkin Elmer Biosystems 9700 block thermocycler, essentially as described above. PCR was performed using primers for the 36B4 housekeeping gene. FIG. 18 shows an agarose gel on which 36B4 PCR products have been electrophoretically separated. It can be seen that for each sample tested, no band is amplified or detected in the "no RT" sample. These results confirm that, even when small tissue samples are used, the Universal RT-coupled PCR method does not amplify any non-mRNA derived products.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCE LIST

Getting Rid of Contaminating DNA. Ambion Tech Notes Newsletter. Volume 8, Number 1, 2001.

Bauer P, Rolfs A, Regitz-Zagrosek V, Hildebrandt A, Fleck E. Use of manganese in RT-PCR eliminates PCR artifacts resulting from DNase digestion. BioTechniques 22:1128–32, 1997.

Bustin S A. Absolute quantitation of mRNA using real-time reverse transcription polymerase chain reaction assays (review). J Molec Endocrin, 25:169–193, 2000.

Cantlay A M, Smith C A D, Wallace W A, Yap P-L, Lamb D, Harrison D J. Heterogeneous expression and polymorphic genotype of glutathione S-transferase in human lung. Thorax 49:1010–1014, 1994.

Caruthers, M H, Matteucci, M D, Process for preparing polynucleotides U.S. Pat. No. 4,458,066.

DeRisi J, Penland L, Brown P O, Bittner M L, Meltzer P S, Ray M, Chen Y, Su YA, Trent J M. "Use of a cDNA microarray to analyze gene expression patterns in human cancer", Nat Genet 14:457–460, 1996.

Fodor, S P A, Pirrung, M C, Read, Leighton, J, Stryer, L. Synthesis and screening of immobilized oligonucleotide arrays U.S. Pat. No. 5,510,270.

Fodor S P, Read J L, Pirrung M C, Stryer L, Lu AT, Solas D. Light-directed, spatially addressable parallel chemical synthesis Science 251: 767–73, 1991.

Folz R J, Nepluev I. Poly(A) cDNA-specific (PACS) RT-PCR: A quantitative method for the measurement of any poly(A)-containing mRNA not affected by contaminating genomic DNA. Biotechniques 29:762–768, 2000.

Friend, S H. Methods of determining protein activity levels using gene expression profiles, U.S. Pat. No. 6,324,479.

Hartel C, Bein G, Kirchner H, Kluter H. A Human Whole-Blood Assay for Analysis of T-Cell Function by Quantification of Cytokine mRNA. Scandinavian Journal of Immunology 49,649–654, 1999.

Heller; M J. Active programmable electronic devices for molecular biological analysis and diagnostics U.S. Pat. No. 5,605,662.

Huang Z, Fasco M J, Kaminsky L S. Optimization of DNase I Removal of Contaminating DNA from RNA for Use in Quantitative RNA-PCR. BioTechniques Vol. 20, No 6,1012–20, 1996.

Ivarsson K, Weijdegard B. Evaluation of the effects of DNase treatment on signal specificity in RT-PCR and in situ RT-PCR. BioTechniques 25:630–36, 1998.

Joo C H, Lee H, Kim E, Lee B, Cho Y K, Kim K. Differential amplifying RT-PCR: a novel RT-PCR method to differentiate mRNA from its DNA lacking intron. J. Virol. Meth. 100:71–81, 2002.

Krauter J, Wattjes M P, Nagel S, Heidenreich O, Krug U, Kafert S, Bunjes D, Bergmann L, Ganser A, Heil G. Real-time RT-PCR for the Detection and Quantification of AML1/MTG8 Fusion Transcripts in t (8:21)-Positive AML Patients. British Journal of Haematology 107,80–85, 1999.

Kreuzer K-A, Lass U, Landt O, Nitsche A, Laser J, Ellerbrok H, Pauli G, Huhn D, Schmidt C A. Highly Sensitive and Specific Fluorescence Reverse Transcription-PCR Assay for the Pseudogene-free Detection of B-Actin Transcripts as Quantitative Reference. Clinical Chemistry 45(2), 1999.

Lacave R, Coulet F, Ricci S, Touboul E, Flahaul A, Rateau J G, Cesari D, Lefranc J P, Bernaudin J F. Comparative Evaluation by Semiquantitative Reverse Transcriptase Polymerase Chain Reaction of MDR1, MRP and GSTp Gene Expression in Breast Carcinomas. British Journal of Cancer 77(5) 694–702, 1998.

Leavitt J, Gunning P, Porreca P, NG S-Y, Lin C-S, Kedes L. Molecular cloning and characteristics of mutant and wild type B-actin alleles. Molecular and Cellular Biology, 4:1961–69, 1984.

Liang, P. & Pardee, A. B. Differential display of eukaryotic messenger RNA by means of the polymerase chain reaction [see comments]. Science 257, 967–71, 1992.

Linsley, P S, Schelter, J M. RNA amplification method. U.S. Pat. No. 6,271,002.

Lion T. Current recommendations for positive controls in RT-PCR assays. Leukemia 15, 1033–1037, 2001.

Lipshutz R J, Fodor S P, Gingeras T R, Lockhart D J. High density synthetic oligonucleotide arrays. Nat. Genet. 21(1 Suppl):20–4), 1999.

Lockhart, D J, Vetter, D, Diggelmann, M. Surface-bound, unimolecular, double-stranded DNA U.S. Pat. No. 5,556,752.

Lockhart D J, Dong H, Byrne M C, Follettie M T, Gallo M V, Chee M S, Mittmann M, Wang C, Kobayashi M, Horton H, Brown E L. Expression monitoring by hybridization to high-density oligonucleotide arrays. Nature Biotechnol. 14:1675–80, 1996.

Mandecki; W. Multiplex assay for nucleic acids employing transponders U.S. Pat. No. 6,001,571

Maskos and Southern. Oligonucleotide hybridizations on glass supports: a novel linker for oligonucleotide synthesis and hybridization properties of oligonucleotides synthesized in situ, Nucleic Acids Res. 20:1679–1684, 1992.

Maskos U, Southern E M. A novel method for the parallel analysis of multiple mutations in multiple samples Nucl. Acids Res. 21: 2269–70, 1993.

McGall G, Labadie J, Brock P, Wallraff G, Nguyen T, Hinsberg W. Light-directed synthesis of high-density oligonucleotide arrays using semiconductor photoresists. Proc. Natl. Acad. Sci. (USA) 93: 13555–60, 1996.

Mighell A J, Smith N R, Robinson P A, Markham A F. Vertebrate Pseudogenes. FEBS Letters 468:109–114, 2000.

NG S-Y, Gunning P, Eddy R, Ponte P, Leavitt J , Shows T, Kedes L. Evolution of the functional human B-actin gene and its multipseudogene family. Molecular and Cellular Biology 5(10):2720–32, 1985.

Overbergh L, Valckx D, Waer M, Mathieu C. Quantification of Murine Cytokine mRNAs Using Real Time Quantitative Reverse Transcriptase PCR. Cytokine, Vol 11(4): 305–312, 1999.

Pease A C, Solas D, Sullivan E J, Cronin M T, Holmes C P, Fodor S P. Light-generated oligonucleotide arrays for rapid DNA sequence analysis. Proc. Natl. Acad. Sci. USA 91:5022–5026, 1994.

Pirrung, M C, Read, J L, Fodor, S P A, Stryer, L. Large scale photolithographic solid phase synthesis of polypeptides and receptor binding screening thereof. U.S. Pat. No. 5,143,854

Raff T, van der Giet M, Endemann D, Wiederholt T, Paul M. Design and testing of β-actin primers that do not co-amplify processed pseudogenes. BioTechniques 23:456–460, 1997.

Schena M, Shalon D, Davis R W, Brown P O. Quantitative monitoring of gene expression patterns with a complementary DNA microarray. Science 1995 Oct 20;270(5235):467–70.

Schena M, Shalon D, Heller R, Chai A, Brown P O, Davis R W. Parallel human genome analysis; microarray-based expression of 1000 genes, Proc. Natl. Acad. Sci. USA 93:10539–11286, 1996.

Shalon D, Smith S J, Brown P O. A DNA microarray system for analyzing complex DNA samples using two-color fluorescent probe hybridization. Genome Res. 6:639–645, 1996.

Shibutani M, Uneyama C, Miyazaki K, Toyoda K, Hirose M. Methacarn Fixation: A Novel Tool for Analysis of Gene Expression in Paraffin-Embedded Tissue Specimens. Laboratory Investigation Vol. 80, No 2 , p. 199, 2000.

Shuldiner A R, Nirula A, Roth J. RNA template-specific PCR: polymerase chain reaction (RS-PCR): a novel strategy to reduce dramatically false positives. Gene 91: 139–142, 1990.

Shuldiner A R, Tanner K, Moore C, Roth J. RNA template-specific PCR: An improved method that dramatically reduces false positives in RT-PCR. BioTechniques 11(6): 760–763, 1991.

Smith R D, Ogden C W, Penny M A. Exclusive amplification of cDNA template (EXACT) RT-PCR to avoid amplifying contaminating genomic pseudogenes. Biotechniques 31:776–782, 2001;

Stern, D. System and methods for detection of labeled materials U.S. Pat. No. 6,207,960.

Sybesma W, Hugenholtz J, Mierau I, Kleerebezam M. Improved efficiency and reliability of RT-PCR using tag-extended RT primers and temperature gradient PCR. BioTechniques 31:466–472, 2001.

Taylor J J, Heasman T. Raff, M. van der Giet, D. Endemann, T. Wiederholt and M. Paul. Design and Testing of B-Actin PA. Control genes for reverse transcriptase/polymerase chain reaction (RT-PCR). Br J Haematolog 86: 444–5, 1994.

Traver R D, Siegel D, Beall H D, Phillips R M, Gibson N W, Franklin W A, Ross D. Characterization of a polymorphisim in NAD(P)H: quinone oxidoreductase (DT-diaphorase). British Journal of Cancer 75(1), 69–75, 1997.

Trulson, M., Stern, D, Fiekowsky, P, Rava, R, Walton, I, Fodor; S P A. Method and apparatus for imaging a sample on a device U.S. Pat. No. 5,578,832.

Trummer A, Kadar J, Arsenivev L, Petersen D, Ganser A, Lichtinhagan R. Competitive Cytokeratin 19 RT-PCR for Quantification of Breast Cancer Cells in Blood Suspensions. Journal of Hematotherapy & Stem Cell Research 9:275–284, 2000.

Voet D, Voet J G. *Biochemistry.* Second edition, John Wiley & Sons, New York, 1995. pgs 950–951.

Yershov G, Barsky V, Belgovskiy A, Kirillov E, Kreindlin E, Ivanov I, Parinov S, Guschin D, Drobishev A, Dubiley S, Mirzabekov A. DNA analysis and diagnostics on oligonucleotide microchips. Proc. Natl. Acad. Sci. USA, 93(10):4913–4918, 1996.

What is claimed is:

1. A Universal reverse transcription (RT) primer having the formula 3'-NVVT$_n$X-5', wherein N is equal to all base combinations, V=A, C, or G, n=16–26 and X has the nucleotide sequence 5'-AAC GAG ACG ACG ACA GAC-3' (SEQ ID No. 20).

2. A Universal reverse transcription (RT) primer according to claim 1, wherein n=21.

3. A primer set comprising a Universal reverse transcription (RT) primer having the formula 3'-NVVT$_n$X-5', wherein N is equal to all base combinations, V=A, C, or G, n=16–26 and X has the nucleotide sequence 5'-AAC GAG ACG ACG ACA GAC-3' (SEQ ID No. 20).

4. A primer set having the formula 3'-NVVT$_n$X-5', wherein N is equal to all base combinations, V=A, C or G, n=16–26, X having the nucleotide sequence 5'-AAC GAG ACG ACG ACA GAC-3' (SEQ ID No. 20), a forward primer and at least one reverse primer identical to X.

5. The primer set according to claim 3, wherein n=21.

6. The primer set according to claim 4, wherein n=21.

7. A method of reverse transcribing mRNA to produce cDNA, comprising reverse transcribing mRNA with the Universal reverse transcription (RT) primer of claim 1, wherein X remains unbound to said mRNA but is integrated into each cDNA molecule synthesized, thereby 5' tagging mRNA-derived cDNAs with sequence X.

8. A method of selectively detecting a mRNA-derived cDNA, wherein genomic DNA detection is avoided, comprising:
   a) reverse transcribing mRNA to produce cDNA according to claim 7,
   b) using said cDNA as template in a PCR reaction,
   c) using a forward and a reverse primer to amplifying a sequence present in said cDNA, and
   d) detecting the amplified sequence produced in said PCR reaction.

9. The method according to claim 7, wherein n=21.

10. The method according to claim 8, wherein n21.

11. A method for constructing a cDNA library from a population of mRNA molecules, comprising conducting reverse transcription (RT) PCR with the primer set of claim 4, whereby amplification of a plurality of mRNAs is achieved, and wherein amplification of genomic DNA is avoided.

12. The method according to claim 8, wherein n=21.

13. A method according to claim 11, wherein the mRNA or cDNA is derived from the group consisting of brain, spleen, bone, heart, vascular, lung, kidney, liver, intestine, muscle, blood, pituitary, endocrine glands, lymph node, epithelia, buccal mucosa, serum, plasma, cerebrospinal fluid, urine, saliva, biopsies, swabs and cytological specimens.

14. A method according to claim 13, wherein the mRNA or cDNA is derived from a cell population, said cell population comprising a single cell, or up to 100 to 1,000,000 cells or more.

15. A kit for selectively detecting mRNA-derived cDNA, wherein genomic DNA detection is avoided, comprising a Universal reverse transcription (RT) primer according to claim 1.

16. A kit for selectively detecting mRNA-derived cDNA, wherein genomic DNA detection is avoided, comprising a Universal reverse primer according to claim 2.

17. A method for obtaining and/or generating gene expression data comprising subjecting a sample to Universal RT-coupled PCR with the primer of claim 1.

18. A method for obtaining and/or generating gene expression data comprising subjecting a sample to Universal RT-coupled PCR with the primer of claim 1 and using an automated data acquisition system.

19. A method of generating gene expression data comprising:

a) receiving a sample from a client,
b) subjecting said sample to RT-coupled PCR with the primer of claim 1,
c) generating gene expression data from said sample, and
d) transmitting said gene expression data to said client.

20. A method for obtaining and/or generating drug efficacy data comprising subjecting a sample to RT-coupled PCR with the primer of claim 1.

21. A method for obtaining and/or generating drug efficacy data with the primer of claim 1 and an automated data acquisition system.

22. A method of generating drug efficacy data comprising:
a) receiving a sample from a client,
b) subjecting said sample to RT-coupled PCR with the primer of claim 1, and
c) transmitting said drug efficacy data to said client.

23. A method for transmitting information comprising performing a method as claimed in any one of claims 7, 8, 9, 10, 11, 12, 13, 14, 17, 18, 19, 20, 21, or 22, and transmitting a result thereof.

24. The method of claim 23 wherein the transmitting is via email or the internet.

25. A PCR primer consisting of a nucleic acid molecule consisting of the sequence set forth in SEQ ID No. 20.

26. A method for amplifying cDNA comprising employing the primer of claim 25 in a PCR.

27. A method for transmitting data comprising performing the method of claim 26 and transmitting a result therefor.

28. The method of claim 27, wherein the transmitting is via internet or e-mail.

* * * * *

UNITED STATES PATENT AND TRADEMARK OFFICE
CERTIFICATE OF CORRECTION

| | |
|---|---|
| PATENT NO. | : 7,141,372 B2 |
| APPLICATION NO. | : 10/342684 |
| DATED | : November 28, 2006 |
| INVENTOR(S) | : Simmon D. Spivack and Gregory J. Hurteau |

Page 1 of 1

It is certified that error appears in the above-identified patent and that said Letters Patent is hereby corrected as shown below:

Column 43, line 66, "amplifying" should read --amplify--.

Signed and Sealed this

Thirteenth Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 7,141,372 B2
APPLICATION NO. : 10/342684
DATED : November 28, 2006
INVENTOR(S) : Simon D. Spivack et al.

It is certified that error appears in the above-identified patent and that said Letters Patent is hereby corrected as shown below:

IN THE SPECIFICATION

Column 1, line 32, please replace the paragraph as follows:

"This work was supported by the government, in part, by grants from the National Institute of Environmental Health Sciences and the National Cancer Institute (NIEHS-K08 ES0029801; NCI-R21 CA94714). The government may have certain rights to this invention."

--This invention was made with government support under ES000298 awarded by the National Institutes of Health. The government has certain rights in the invention.--

Signed and Sealed this
Twenty-fourth Day of April, 2012

David J. Kappos
*Director of the United States Patent and Trademark Office*

SEQUENCE LISTING

```
<160> NUMBER OF SEQ ID NOS: 20
<210> SEQ ID NO 1
<211> LENGTH: 22
<212> TYPE: DNA
<213> ORGANISM: Artificial Sequence
<220> FEATURE:
<223> OTHER INFORMATION: Standard-design forward PCR primer for B-Actin

<400> SEQUENCE: 1
ccacgaaact accttcaact cc                                                  22

<210> SEQ ID NO 2
<211> LENGTH: 25
<212> TYPE: DNA
<213> ORGANISM: Artificial Sequence
<220> FEATURE:
<223> OTHER INFORMATION: Standard-design reverse PCR primer for B-Actin

<400> SEQUENCE: 2
tcatactcct gctgcttgct gatcc                                               25

<210> SEQ ID NO 3
<211> LENGTH: 24
<212> TYPE: DNA
<213> ORGANISM: Artificial Sequence
<220> FEATURE:
<223> OTHER INFORMATION: Standard-design forward PCR primer for GAPDH

<400> SEQUENCE: 3
ggtcggagtc aacggatttg gtcg                                                24

<210> SEQ ID NO 4
<211> LENGTH: 22
<212> TYPE: DNA
<213> ORGANISM: Artificial Sequence
<220> FEATURE:
<223> OTHER INFORMATION: Standard-design reverse PCR primer for GAPDH

<400> SEQUENCE: 4
cctccgacgc ctgcttcacc ac                                                  22

<210> SEQ ID NO 5
<211> LENGTH: 23
<212> TYPE: DNA
```

<213> ORGANISM: Artificial Sequence
<220> FEATURE:
<223> OTHER INFORMATION: Standard-design forward PCR primer for 36B4

<400> SEQUENCE: 5
ctacttcctt aagatcatcc aac                                             23

<210> SEQ ID NO 6
<211> LENGTH: 19
<212> TYPE: DNA
<213> ORGANISM: Artificial Sequence
<220> FEATURE:
<223> OTHER INFORMATION: Standard-design reverse PCR primer for 36B4

<400> SEQUENCE: 6
tcaaagagac caaatccca                                                  19

<210> SEQ ID NO 7
<211> LENGTH: 19
<212> TYPE: DNA
<213> ORGANISM: Artificial Sequence
<220> FEATURE:
<223> OTHER INFORMATION: Standard-design forward PCR primer for CYP1B1

<400> SEQUENCE: 7
gccactatca ctgacatct                                                  19

<210> SEQ ID NO 8
<211> LENGTH: 20
<212> TYPE: DNA
<213> ORGANISM: Artificial Sequence
<220> FEATURE:
<223> OTHER INFORMATION: Standard-design reverse PCR primer for CYP1B1

<400> SEQUENCE: 8
cttgcctctt gcttcttatt                                                 20

<210> SEQ ID NO 9
<211> LENGTH: 20
<212> TYPE: DNA
<213> ORGANISM: Artificial Sequence
<220> FEATURE:
<223> OTHER INFORMATION: Standard-design forward PCR primer for CYP1A1

<400> SEQUENCE: 9
ttccgacact cttccttagt                                                 20

<210> SEQ ID NO 10
<211> LENGTH: 20
<212> TYPE: DNA
<213> ORGANISM: Artificial Sequence
<220> FEATURE:
<223> OTHER INFORMATION: Standard-design reverse PCR primer for CYP1A1

<400> SEQUENCE: 10
atggttagcc catagatggg                                                 20

<210> SEQ ID NO 11
<211> LENGTH: 20
<212> TYPE: DNA
<213> ORGANISM: Artificial Sequence
<220> FEATURE:
<223> OTHER INFORMATION: Standard-design forward PCR primer for GST-M1

<400> SEQUENCE: 11
actttcccaa tctgccctac                                                 20

<210> SEQ ID NO 12
<211> LENGTH: 20
<212> TYPE: DNA
<213> ORGANISM: Artificial Sequence
<220> FEATURE:
<223> OTHER INFORMATION: Standard-design reverse PCR primer for GST-M1

<400> SEQUENCE: 12
ttctggattg tagcagatca                                        20

<210> SEQ ID NO 13
<211> LENGTH: 21
<212> TYPE: DNA
<213> ORGANISM: Artificial Sequence
<220> FEATURE:
<223> OTHER INFORMATION: Standard-design forward PCR primer for GST-P1

<400> SEQUENCE: 13
caccaactat gaggcgggca a                                      21

<210> SEQ ID NO 14
<211> LENGTH: 19
<212> TYPE: DNA
<213> ORGANISM: Artificial Sequence
<220> FEATURE:
<223> OTHER INFORMATION: Standard-design reverse PCR primer for GST-P1

<400> SEQUENCE: 14
atcagcagca agtccagca                                         19

<210> SEQ ID NO 15
<211> LENGTH: 22
<212> TYPE: DNA
<213> ORGANISM: Artificial Sequence
<220> FEATURE:
<223> OTHER INFORMATION: Transcript-specific forward primer of the
      forward-Universal reverse PCR primer pair for GST-M1

<400> SEQUENCE: 15
catgatctgc tacaatccag aa                                     22

<210> SEQ ID NO 16
<211> LENGTH: 20
<212> TYPE: DNA
<213> ORGANISM: Artificial Sequence
<220> FEATURE:
<223> OTHER INFORMATION: Transcript-specific forward primer of the
      forward-Universal reverse PCR primer pair for GST-P1

<400> SEQUENCE: 16
tctccttcgc tgactacaac                                        20

<210> SEQ ID NO 17
<211> LENGTH: 18
<212> TYPE: DNA
<213> ORGANISM: Artificial Sequence
<220> FEATURE:
<223> OTHER INFORMATION: Transcript-specific forward primer of the
      forward-Universal reverse PCR primer pair for B-Actin

<400> SEQUENCE: 17
gccatcctaa aagccacc                                          18

<210> SEQ ID NO 18
<211> LENGTH: 20

```
<212> TYPE: DNA
<213> ORGANISM: Artificial Sequence
<220> FEATURE:
<223> OTHER INFORMATION: Transcript-specific forward primer of the
      forward-Universal reverse PCR primer pair for GAPDH

<400> SEQUENCE: 18
gcacaagagg aagagagaga                                              20

<210> SEQ ID NO 19
<211> LENGTH: 20
<212> TYPE: DNA
<213> ORGANISM: Artificial Sequence
<220> FEATURE:
<223> OTHER INFORMATION: Transcript-specific forward primer of the
      forward-Universal reverse PCR primer pair for 36B4

<400> SEQUENCE: 19
gacaatggca gcatctacaa                                              20

<210> SEQ ID NO 20
<211> LENGTH: 18
<212> TYPE: DNA
<213> ORGANISM: Artificial Sequence
<220> FEATURE:
<223> OTHER INFORMATION: Universal reverse transcription primer

<400> SEQUENCE: 20
aacgagacga cgacagac                                                18
```